US009993005B2

(12) United States Patent
Pierce

(10) Patent No.: US 9,993,005 B2
(45) Date of Patent: Jun. 12, 2018

(54) PREVENTING OR DELAYING CHILL INJURY RESPONSE IN PLANTS

(71) Applicant: GEORGIA STATE UNIVERSITY RESEARCH FOUNDATION, INC., Atlanta, GA (US)

(72) Inventor: George E. Pierce, Canton, GA (US)

(73) Assignee: Georgia State University Research Foundation, Inc., Atlanta, GA (US)

( * ) Notice: Subject to any disclaimer, the term of this patent is extended or adjusted under 35 U.S.C. 154(b) by 110 days.

(21) Appl. No.: 14/773,811

(22) PCT Filed: Mar. 12, 2014

(86) PCT No.: PCT/US2014/024491
§ 371 (c)(1),
(2) Date: Sep. 9, 2015

(87) PCT Pub. No.: WO2014/159628
PCT Pub. Date: Oct. 2, 2014

(65) Prior Publication Data
US 2016/0015039 A1 Jan. 21, 2016

Related U.S. Application Data

(60) Provisional application No. 61/783,047, filed on Mar. 14, 2013.

(51) Int. Cl.
*A01N 63/00* (2006.01)
*A01N 63/02* (2006.01)

(52) U.S. Cl.
CPC .............. *A01N 63/00* (2013.01); *A01N 63/02* (2013.01)

(58) Field of Classification Search
CPC .......... A01N 63/02; A01N 63/00; A01H 3/00; A01H 3/04; C12N 1/20; C12N 1/38; C12N 11/06; C12N 11/10; C12N 11/12; C12N 9/80; C12N 9/82; C12N 9/88; C12N 9/96; C12R 1/01; C12Y 305/05; C12Y 401/99; C12Y 404/1009
See application file for complete search history.

(56) References Cited

U.S. PATENT DOCUMENTS

| | | | |
|---|---|---|---|
| 3,940,316 A | 2/1976 | Commeyras et al. |
| 4,001,081 A | 1/1977 | Commeyras et al. |
| 4,343,900 A | 8/1982 | Watanabe |
| 4,880,739 A | 11/1989 | Yamada et al. |
| 5,089,411 A | 2/1992 | Yamada et al. |
| 5,409,509 A | 4/1995 | Burth et al. |
| 5,512,466 A | 4/1996 | Klee et al. |
| 5,545,815 A | 8/1996 | Fischer et al. |
| 5,664,368 A | 9/1997 | Sandor |
| 5,807,730 A | 9/1998 | Ito et al. |
| 5,863,750 A | 1/1999 | Pierce |
| 6,060,265 A | 5/2000 | Pierce |
| 6,132,985 A | 10/2000 | Pierce |
| 6,133,001 A | 10/2000 | Homann et al. |
| 6,133,421 A | 10/2000 | Fallon et al. |
| 6,153,415 A | 11/2000 | Oriel et al. |
| 6,156,956 A | 12/2000 | Theoglis et al. |
| 6,194,193 B1 | 2/2001 | Drahos et al. |
| 6,214,603 B1 | 4/2001 | Oriel et al. |
| 6,228,633 B1 | 5/2001 | Oriel et al. |
| 6,242,242 B1 | 6/2001 | Oriel et al. |
| 6,251,388 B1 | 6/2001 | Durden |
| 6,287,828 B1 | 9/2001 | Oriel et al. |
| 6,316,242 B1 | 11/2001 | Endo et al. |
| 6,426,105 B1 | 7/2002 | Palta et al. |
| 6,524,998 B1 | 2/2003 | Kloepper et al. |
| 6,606,822 B2 | 8/2003 | Bonfiglio |
| 6,613,435 B1 | 9/2003 | Guritza |
| 6,649,397 B1 | 11/2003 | Nakamura |
| 6,677,149 B2 | 1/2004 | Dicosimo et al. |
| 6,730,508 B1 | 5/2004 | Ito et al. |
| 6,735,902 B1 | 5/2004 | Ahm |
| 6,955,911 B2 | 10/2005 | Ryuno et al. |
| 6,995,007 B2 | 2/2006 | Gunner et al. |
| 7,084,321 B2 | 8/2006 | Pais et al. |
| 7,213,366 B1 | 5/2007 | Ahm |

(Continued)

FOREIGN PATENT DOCUMENTS

| | | |
|---|---|---|
| CN | 1384709 | 12/2002 |
| CN | 1547609 | 11/2004 |

(Continued)

OTHER PUBLICATIONS

Official Action issued in Russian Application No. 2013105714/10(008509), dated Dec. 14, 2016.
Gonzalez-Aguilar, et al., "Methyl jasmonate treatments reduce chilling injury and activate the defense response of guava fruits", Biochemical and Biophysical Research Communications, Academic Press Inc., vol. 313, No. 3, 2004, pp. 694-701.
Pierce, et al., "Preliminary report on a catalyst derived from induced cells of strain DAP 96253 that delays the ripening of selected climacteric fruit: bananas, avocados, and peaches", Journal of Industrial Microbiology & Biotechnology; Official Journal of the Society for Industrial Microbiology, vol. 38, No. 9, 2011, pp. 1567-1573.
Communication Pursuant to Rule 164(1) EPC in EP 14773615.1, dated Jul. 6, 2016.
Alexander and Grierson, "Ethylene biosynthesis and action in tomato: a model for climacteric fruit ripening" J. Exp. Botany, 53:2039-55 (2002).
Avni et al., "Induction of ethylene biosynthesis in Nicotiana tabacum by a Trichoderma viride sylanase is correlated to the accumulation of 1-aminocyclopropane-1-carboxylic acid (ACC) synthase and ACC oxidase transcripts" Plant Physiol. 106:1049-55 (1994).
Badr et al., "Kinetics and properties of L-glutaminase and L-asparaginase activities of Pseudomonas ovalis," Badt. II. Abt. 131:489-96 (1976).

(Continued)

*Primary Examiner* — Lisa J Hobbs
(74) *Attorney, Agent, or Firm* — Thomas | Horstemeyer, LLP

(57) ABSTRACT

Provided are methods and compositions for preventing or delaying a chill injury response of a plant or plant part that exhibits a chill injury response. The methods comprise exposing the plant or plant part to one or more bacteria, one or more enzymes, and/or an enzymatic extract isolated from one or more bacteria. The one or more bacteria, one or more enzymes, and/or the enzymatic extract isolated from one or more bacteria are exposed to the plant or plant part in a quantity sufficient to prevent or delay the chill injury response of the plant or plant part.

19 Claims, 6 Drawing Sheets

(56) References Cited

U.S. PATENT DOCUMENTS

| | | | |
|---|---|---|---|
| 7,244,595 | B2 | 7/2007 | Uehara et al. |
| 7,405,064 | B2 | 7/2008 | Payne et al. |
| 7,504,557 | B2 | 3/2009 | Gallie et al. |
| 7,531,343 | B2 | 5/2009 | Pierce et al. |
| 7,531,344 | B2 | 5/2009 | Pierce et al. |
| 2002/0139046 | A1 | 10/2002 | Weber et al. |
| 2003/0044807 | A1 | 3/2003 | Bramucci et al. |
| 2003/0049807 | A1 | 3/2003 | Salvo et al. |
| 2003/0084609 | A1 | 5/2003 | Perriello et al. |
| 2003/0093946 | A1 | 5/2003 | Gutierrez Pavez |
| 2003/0115633 | A1 | 6/2003 | Pais et al. |
| 2004/0072694 | A1 | 4/2004 | Jacobson et al. |
| 2004/0106165 | A1 | 6/2004 | Reisinger et al. |
| 2005/0000154 | A1 | 1/2005 | Perriello et al. |
| 2005/0014243 | A1 | 1/2005 | Uehara et al. |
| 2005/0066389 | A1 | 3/2005 | Gallie et al. |
| 2005/0227356 | A1 | 10/2005 | Lessard et al. |
| 2007/0068072 | A1 | 3/2007 | Xavier et al. |
| 2007/0090122 | A1 | 4/2007 | Zeypang |
| 2007/0184528 | A1 | 8/2007 | Pierce |
| 2007/0184543 | A1 | 8/2007 | Pierce |
| 2007/0259783 | A1 | 11/2007 | Tateishi et al. |
| 2008/0236038 | A1 | 10/2008 | Pierce et al. |
| 2011/0183847 | A1* | 7/2011 | Pierce .................. A01H 3/00 504/117 |
| 2013/0035232 | A1* | 2/2013 | Pierce .................. A01H 3/00 504/117 |

FOREIGN PATENT DOCUMENTS

| | | |
|---|---|---|
| EP | 0109083 | 9/1986 |
| EP | 0243966 | 6/1988 |
| EP | 0243967 | 6/1988 |
| EP | 0307926 | 3/1989 |
| EP | 0362829 | 4/1990 |
| EP | 0790310 | 8/1997 |
| JP | 54129190 | 10/1979 |
| JP | 5030982 | 2/1993 |
| JP | 5030983 | 2/1993 |
| JP | 8056684 | 3/1996 |
| JP | 8154691 | 6/1996 |
| JP | 8187092 | 7/1996 |
| JP | 08196208 | 8/1996 |
| JP | 2000-000470 | 7/2000 |
| JP | 5236977 | 7/2013 |
| PL | 161863 | 8/1993 |
| RU | 829484 | 5/1981 |
| WO | 1992012249 | 7/1992 |
| WO | 1999040177 | 8/1999 |
| WO | 2000036085 | 6/2000 |
| WO | 2000051435 | 9/2000 |
| WO | 2002072856 | 9/2002 |
| WO | 2003037066 | 5/2003 |
| WO | 2003041491 | 5/2003 |
| WO | 2007090122 | 8/2007 |
| WO | 2008124307 | 10/2008 |
| WO | 2011091374 | 7/2011 |
| WO | 2013019604 | 2/2013 |

OTHER PUBLICATIONS

Bahr and Bonner, Jr., "Cyanide-insensitive respiration" J. Biol. Chem. 248: 3446-50 (1973).
Bates and Warner, "1-MCP and Fruit Quality," Perishables Handling Quarterly, Issue No. 108, (Nov. 2001) postharvest.ucdavis.edu/datastorefiles/234-37.pdf.
Beaudoin et al., "Interactions between abscisic acid and ethylene signaling cascades," The Plant Cell 12:1103-15 (2000).
Bijnen et al., "Geometrical optimization of a longitudinal resonant photoacoustic cell for sensitive and fast trace gas detection" Rev. Sci. Instrum. 67: 2914-23 (1996).
Blankenship and Dole, "1-Methylcyclopropene: a review." Postharvest Biol. Technol. 28:1-25 (2003).
Bleecker and Kende, "Ethylene: a gaseous signal molecule in plants." Ann. Rev. Cell. Dev. Biol. 16:1 - 18 (2000).
Bowyer and Wills, "Delaying postharvest senescence of cut flowers using nitric oxide," Rural Industries Research and Development Corporation, (May 2003). www.rirdc.gov.au/reports/WNP/03-015.pdf.
Bucke, C., "Cell Immobilization in Calcium Alginate," Methods in Enzymology, vol. 135, 1987, pp. 175-189.
Bunch et al., "Biotransformation of nitriles by Rhodococci" Antonie van Leeuwenhoek, Kluwer Academic Publishers, The Netherlands 74:89-97 (1998).
Cai et al., Study on Immobilization of the Cell of Niteile Hydratase by Flocculation, Chemical Technology Market, 3:39-42 (2005).
Caron, Environmental Test Chambers, http://www.caronproducts.com/I8/prodcat/all.
Chamani et al., "Ethylene and anti-ethylene treatment effects on cut 'First Red' rose," Journal of Applied Horticulture, 7(1): 3-7 (2005).
"Chiquita explores financial alternatives," Refrigerated Transporter, Sep. 29, 2006, http://refrigeratedtrans.com/marr/transpoation_chiquita_explores_financial/index.html.
Cincinnati Sub-zero, Microclimate Benchtop Test Chambers, http://www.cszindustrial.com/products/microclimate/microclimate.
Colby et al., Immobilization of Rhodococcus AJ270 and Use of Entrapped Biocatalyst for the Production of Acrylic Acid, Monatshefte für Chemice, 131:655-666 (2000).
Collins, et al., "The Utilization of Nitriles and Amides by *Nocardia rhodochrous*," J. Gen Microbiol., vol. 129, 1983, pp. 711-718.
Crassweller, Pennsylvania State University, Horticulture 432, Lecture Notes: Thinning and PGRs, (2000). www.hortweb.cas.psu.edu/courses/hort432/lecturenotes/pgr.html.
Crisoto, "Stone fruit maturity indices: a descriptive review," Postharvest News and Information 5(6):65N-68N (1994).
Cristescu et al., "Ethylene production by Botrytis cinerea in vitro and in tomatoes." Appl. Environ. Microbial. 68:5342-50 (2002).
Curry and Thompson, "Delicious quality can be affected by ethephon or ReTain," Washington University—Tree Fruit Research and Extension Center: Postharvest Information Network, 15th Annual Postharvest Conference, Mar. 9-10, (1999). http://postharvest.tfrec.wsu.edu/pgDisplay.php?article=PC99A.
Difco Manual of Dehydrated Culture Media and Reagents for Microbiological and Clinical Laboratory Procedures, 9th Ed., 1953, pp. 264-265.
Dixon and Palva, "Stress-induced phenylpropanoid metabolism." Plant Cell. 7:1085-97 (1995).
Dole Worldwide: Latin America and Caribbean, http://www.dole.com/CompanyInfo/About/Worldwide/LatinAmerica.isp.
Dominguez et al., "Effect of inhibitors of ethylene biosynthesis and action on ripening of bananas." Proc. Int. Symp. Bananas in Subtropics (V. Galan Sauco, Editor) 519-28 (1998).
Dong et al., "Purification and characterization of 1-aminocyclopropane-1-carboxylate oxidase from apple fruit," Proc. Natl. Acad. Sci. USA, 89:9789-93 (1992).
El-Sharkawy et al., "Isolation and characterization of four ethylene perception elements and their expression during ripening in perars (*Pyrus communis* L.) with/without cold requirement." J Exp. Botany. 54:1615-25 (2003).
Fawcett et al., "A Rapid and Precise Method for the Determination of Urea", J. Clin. Path. 13:156-9 (1960).
Ferreira, J., et al., "Comparison of three different methods for trehalose determination in yeast extracts," Food Chemistry, vol. 60, No. 2, pp. 251-254.
Fisher et al., "Bacillus subtilis 168 contains two differentially regulated genes encoding L-asparaginase" J. Bacteriol. 184(8):2148-54 (2002).
Floratech, Tips on Keeping Flowers Healthy, http://www.floratech.net/New/%C2%BFmode=view_page&page_id=20.html.
Foda et al., "Formation and properties of L-glutaminase and L-asparaginase activities in Pichia polymorpha," Acta Microbiol. Pol. 29(4):343-52 (1980).
Fournand et al., "Acyl transfer activity of an amidase from *Rhodococcus* sp. Strain R312: Formation of a wide range of hydroxamic acids" Applied and Environmental Microbiology 64(8):2844-52 (1998).

(56) References Cited

OTHER PUBLICATIONS

Frankenberger WT and Tabatabai MA. Amidase and urease activities in plants. Plant and Soil 1982, 64(2):153-166.

Gas Control Systems, Ethylene Analyser GCS-560, www.gascontrolsvstems.com.

GEO-PIE Project: Delayed fruit ripening, www.geopie.cornell.edu~traits/fruitrip.html.

Goda et al., "Discovery of a novel enzyme, isonitrile hydratase, involved in nitrogen-carbon triple bond cleavage" J. Biol. Chem. 276(26):23480-5 (2001).

Hann et al., "5-Cyanovaleramide Production Using Immobilized Pseudomonas Chlororaphis B23", Bioorg. Medicinal Chem., 7:2239-45 (1999).

Harper, D., "Characterization of a Nitrilase from Nocardia sp. (Rhodochrous Group) N.C.I.B. 11215, Using p-Hydroxybenzonitrile as Sole Carbon Source," Int. J. Biochem, vol. 17, No. 6, 1985, pp. 677-683.

Harper, D., "Microbial metabolism of aromatic nitriles," Enzymology of C-N cleavage by Nocardia sp. (Rhodochrous group) N.C.I.B. 11216, Biochem J., vol. 165, No. 2, 1977, pp. 309-319.

Hong, J. H., & Gross, K. C. (2000). Involvement of ethylene in development of chilling injury in fresh-cut tomato slices during cold storage. Journal of the American Society for Horticultural Science, 125(6), 736-741.

Huber et al., "Use of 1-methylcyclopropene (1-MCP) on tomato and avocado fruits: potential for enhanced shelf life and quality retention," University of Florida, IFAS Extension, (2003). http://edis.ifas.ufl.edu/HS151.

International Labour Organization, "The world cut flower industry: trends and prospects," http://www.ilo.org/public/englishldialoue/sector/papers/ctflower/139e2.htm.

Itai et al., "Rapid identification of 1 -minocyclopropane- 1 -carboxylate (ACC) synthase genotypes in cultivars of Japanese pear (Pyruspyrifolia Nakai) using CAPS markers." Theor. Appl. Genet. 106:1266- 72 (2003).

Johnson and Ecker, "The ethylene gas signal transduction pathway: a molecular perspective." Ann. Rev. Genetics. 32: 227-54 (1998).

Jun, C., "Study on Immobilization of the Cells of Niteile Hydratase by Flocculation," Chemical Technology Market, vol. 3, 2005, pp. 39-42.

Kader, "A summary of CA requirements and recommendations for fruits other than apples and pears," Postharvest Horticulture Series No. 22A, University of California, Davis, pp. 29-70 (2001).

Kader et al., "Postharvest handling and physiology of horticultural crops: a list of selected references," University of California Post-harvest Group (May 2001).

Kato et al., "Nitrile hydratase involved in aldoxime metabolism from Rhodococcus sp. strain YH3-3 purification and characterization" Eur. J. Biochem. 263(3):662-70 (1999).

Kerr, Jonathan R., Bacterial inhibition of fungal growth and pathogenicity; Microbial Ecology in Health and Disease 1999, vol. 11, No. 3, pp. 129-142.

Klee et al., "Control of ethylene synthesis by expression of a bacterial enzyme in transgenic tomato plants." Plant Cell. 3:1187-93 (1991).

Kobayashi, M., et al., "Versatile nitrilases: Nitrile-hydrolysing enzymes," FEMS Microbiology, vol. 120, 1994, pp. 217-224.

Kobayashi, M., et al., "Metalloenzyme nitrile hydratase: Structure, regulation and application to biotechnology," Nature Biotechnology, vol. 16, 1998, pp. 733-736.

Kameda et al., "Characterization of the gene cluster of high-molecular-mass nitrile hydratase (H-NHase) induced by its reaction produce in Rhodococcus rhodochrous J1" Proc. Natl. Acad. Sci. USA 93:4267-72 (1996).

Kopf et al., "Key Role of Alkanoic Acids on the Spectral Properties, Activity, and Active-Site Stability of Iron-Containing Nitrile Hydratase From Brevibacterium R312" Eur J. Biochem. 240:239-44 (1996).

Kozdroj et al., "Influence of introduced potential biocontrol agents on maize seedling gorwth and bacterial community structure in the rhizosphere" Soil Biol. Biochem. 36(11):1775-84 (2004).

Kulayeva, Ethylene in the life of plants, Soros Educational J., 11:78-84 (1998).

Kulikova et al., "Ethylene epoxidation by native and immobilized cells of the propane-assimilating culture Rhodococcus erythropolis 3/89," Prikladnaya Biokhima I Mikrobiologiya 35(6):611-15 (1999).

Lafuente et al., "Phenylalanine ammonia-lyase as related to ethylene in the development of chilling symptoms during cold storage of citrus fruit." J. Agric. Food Chem. 49:6020-5 (2001).

Lawton et al., "Regulation of senescence-related gene expression in carnation flower petals by ethylene," Plant Physiol. 93:1370-5 (1990).

Liao et al., "Postharvest life of cut rose flowers as affected by silver thiosulfate and sucrose," Bot. Bull. Acad. Sin. 41:299-303 (2000).

Linton, E., et al., "Utilization of Aliphatic Amides and Nitriles by Nocardia rhodochrous LL100-21," Journal of General Microbiology, vol. 132, 1986, pp. 1493-1501.

López-Gallego, F., et al., "Enzyme stabilization by glutaraldehyde crosslinking of adsorbed proteins on aminated supports," Journal of Biotechnology, vol. 119, 2005, pp. 70-75.

Mafra et al., Ripening-related changes in the cell walls of olive (Olea europea L.) pulp of two consecutive harvests, J. Sci. Food Agric. 86:988-98 (2006).

Marcos et al., "Involvement of ethylene biosynthesis and perception in the susceptibility of citrus fmits to Penicillium digitatum infection and the accumulation of defence-related mRNAs." J. Exp. Botany. 56: 2183-93 (2005).

Martinkova, et al., "Nitrile- and amide-converting microbial enzymes: stereo-, regio-chemoselecivity" Biocatalysis and Biotransformation 20(2):73-93 (2002).

Mascharak, PK. Structural and functional models of nitrile hydratase. Coordination Chemistry Reviews 2002, 225(1):201-214.

Mathooko, "Regulation of ethylene biosynthesis in higher plants by carbon dioxide," Postharvest Biology and Technology 7:1-26 (1996).

Mayak and Dilley, "Regulation of senescence in carnation (Dianthus caryophyllus): effect of absiscic acid and carbon dioxide on ethylene production," Plant Physiol. 58:663-5 (1972).

Mayak and Halevy, "Interrelationships of ethylene and abscisic acid in the control of rose petal senescence," Plant Physiol. 50:341 -6 (1972).

McDaniel, Virginia Polytechnic University, Horticulture 2164 Lecture Notes, R-8, (1999). http://www.hort.vt.edu/faculty/McDaniel/hort2164/R&DistributionandHandling.htm.

Merritt et al., "Inhibitors of ethylene synthesis inhibit auxin-induce stomatal opening in epidermis detached from leaves of Vicia faba L." Plant Cell Physiol 42:223-30 (2001).

Mullins, University of Florida, BOT 6566 (Plant Growth and Development), Lecture Notes 12: Seed and Fruit Development (2000).

Nagasawa et al., "Optimum Culture Conditions for the Production of Benzonitrilase by Rhodococcus Rhodochrous J1" Arch. Microbiol. 150:89-94 (1988).

Nagasawa, T., et al., "Superiority of Pseudomonas chloroaphis B23 nitrile hydratase as a catalyst for the enzymatic production of acrylamide," Experientia, vol. 45, 1989, pp. 1066-1070.

Nagasawa, T., et al., "The superiority of the third-generation catalyst, Rhodococcus rhodochrous J1 nitrile hydratase, for industrial production of acrylamide," Applied Microbiol. Biotechnol., vol. 40, 1993, pp. 189-195.

Nagasawa et al., "Occurrence of a Cobalt-Induced and Cobalt-Containing Nitrile Hydratase in Rhodococcus Rhodochrous J1" Biochem. Biophys. Res. Comm. 155:1008-16 (1988).

Nagasawa et al., "Characterization of a new cobalt-containing nitrile hydratase purified from urea-induced cells of Rhodococcus rhodochrous J1," Eur. J. Biochem. 196:581-9 (1991).

Nagasawa et al., "Nitrilase of Rhodococcus rhodochrous J1. Conversion into the active form by subunit association" Eur. J. Biochem. 267(1):138-44 (2000).

(56) References Cited

OTHER PUBLICATIONS

Nagasawa, et al., "Optimum culture conditions for the production of cobalt-containing nitrile hydratase by Rhodococcus rhodochrous J1" Applied Microbiology and Biotechnology 34:783-8 (1991).
Nukui et al., "Repressed ethylene production in the gynoecium of longlasting flowers of the carnation 'White Candle': role of the gynoecium in carnation flower senescence," Journal of Experimental Botany 55 (397): 641-50 (2004).
Pandey et al., "Role of polyamines and ethylene as modulators of plant senescence," J. Biosci. 25(3):291-9 (2000).
Pesis et al., Project Abstract, Postharvest delay of fruit ripening by metabolites of anaerobic respiration: acetaldehyde and ethanol. http://www.bard-isus.com/FRAbst/1787.htm.
Pesis and Faiman, "Inhibition of ethylene production and ACC oxidase activity in avocado by acetaldehyde vapours," Proceedings of the World Avocado Congress 111, 354-361, (1995). www.avocadosource.com/WAC3/WAC3 p354.htm.
Plant-Hormones, Ethylene, http://www.plant-hormones.info/ethylene.htm.
Pretel et al., "Ripening and ethylene biosynthesis in controlled atmosphere stored apricots" Eur. Food Res. Technol. 209:130-4 (1999).
Pujade-Renaud et al., "Ehtylene-induced increase in glutamine synthetase activity and mRNA levels in Hevea brasiliensis latex cells" Plant Physiol. 100:131-127 (1994).
Radboud University, Plant hormone ethylene and detection, http://www.ru.nl/tracenasfacility/life_science_trace/plant_physiology/plant_hormone/.
Reed et al., "Delayed ripening tomato plants expressing the enzyme 1-aminocyclopropane-1-carboxylic acid deaminase. 1. Molecular characterization, enzyme expression, and fruit ripening traits," J. Agriculture Food 43:1954-62 (1995).
Rhodes, Purdue University, Horticulture 640—Metabolic Plant Physiology (2008). http://www.hort.purdue.edu/rhodcv/hort640c/sulfate/su00009.htm.
Rychter et al., 1978. "Cyanide-resistant respiration in freshly cut potato slices." Plant Physiol. 61: 667-668.
Sacher, "Permeability characteristics and amino acid incorporation during senescence (ripening) of banana tissue," Plant Physiol. 41:701 -8 (1966).
Saltveit, University of California, Davis. Department of Vegetable Crops. Postharvest Technology Research Information Center [PTRIC] "Respiratory Metabolism" (2006). postharvest.ucdavis.edu.
Sankhian et al., "Nitrile hydratase of Rhodococcus rhodochrous NHB-2: optimization of conditions for production of enzyme and conversion of acrylonitrile to acrylamide" Asian Jr. of Microbiol. Biotech. 5(2):217-33 (2003).
Seong, K-Y., et al., Effect of Trehalose on the Viability of Fluorescent *Pseudomonas*, Strain SSL3, Korean J. Soil Sci. & Fert., vol. 33, No. 4, 2000, pp. 292-301.
Singh et al., "Effect of cobalt, cadmium, and nickel as inhibitors of ethylene biosynthesis on floral malformation, yield, and fruit quality of mango" J. Plant Nutrition. 17:1659-70 (1994).
Singer, M., et al., "Multiple Effects of Trehalose on Protein Folding In Vitro and In Vivo," Molecular Cell, vol. 1, Apr. 1998, pp. 639-648.
Sisler et al., "Inhibition of ethylene responses by 1-methylcyclopropene and 3-methylcycloproene." Plant Growth Reg. 27:105-11 (1999).
Skjerdal OT, et al. "Changes in intracellular composition in response to hyperosmotic stress of NaCl, sucrose or glutamic acid in Brevibacterium lactofermentum and Corynebacterium glutamicum." Applied Microbiology and Biotechnology. Jan. 1996, vol. 44, Issue 5, pp. 635-642.
SLX International, Inc., User manual and instructions for the SLX International, Inc. model 2024 shipping container (2002). SLX International, Inc. San Luis Obispo, CA.

Solomos and Laties, "Similarities between the actions of ethylene and cyanide in initiating the climacteric ripening of avocados" Plant Physiol. 54:506-11 (1974).
Sonawane et al., "Utilization of acidic amino acids and their amides by Pseudomanads: role of periplasmic glutaminase-asparaginase" Arch. Microbiol. 179:151-9 (2003).
Sonawane et al., "Identification of Pseudomonas proteins coordinately induced by acidic amino acids and their amides: a two-dimensional electrophoresis study" Microbiology 149:2909-18 (2003).
Soong et al., "A novel amidase (half-amidase) for half-amide hydrolysis involved in the bacterial metabolism of cyclic imides" Appl. Environ. Microbiol. 66(5):1947-52 (2000).
Sozzi et al., "Gibberellic acid, synthetic auxins, and ethylene differentially modulate a-I,-arabinofwanosidase activities in antisense 1-aminacyclopropane-1-carboxylic acid synthase tomato pericarp discs," Plant Physiol. 129:1330-40 (2002).
ten Have and Woltering, "Ethylene biosynthetic genes are differentially expressed during carnation (*Dianthus caryophyllus* L.) flower senescence" Plant Molec. Biol. 34:89-97 (1997).
Thompson et al., "Acceleration of membrane senescence in cut carnation flowers by treatment with ethylene," Plant Physiol. 69:859-863 (1982).
Trainotti and Casadoro, "Different ethylene receptors show an increased expdression during the ripening of strawberries: does such an increment imply a role for ethylene in the ripening of these non-climateric fruits," J. Exp. Botany 56:2037-46 (2005).
Tucker TM, et al. "A comparison of mycolic acids profiles of Rhodococcus DAP 96253 when grown on different media." Abstracts of the General Meeting of the American Society for Microbiology, vol. 106, 2006, p. 440, & 106th General Meeting of the American-Society-for-Microbiology; Orlando, FL, USA; May 21-25, 2006, available at http://ieg.ou.edu/ASM2006/data/papers/O_100.htm.
Tucker TA, et al. "Effect of growth media on cell envelope composition and nitrile hydratase stability in Rhodococcus rhodochrous strain DAP 96253." J Ind Microbiol Biotechnol. Nov. 2012;39(11):1577-85.
Tudela and Primo-Millo, "1-Aminocyclopropane-1-carboxylic acid transported from roots to shoots promotes leaf abscission in Cleopatra Mandarin (Citrus reshni Hort. ex Tan.) seedlings rehydrated after water stress" Plant Physiology 100:131-7 (1992).
U.S. Biological web page capture, http://www.usbio.net/Product.aspx?ProdSku=P3300, Composition of Peptone, Nov. 2007.
USDA, Agricultural Export Transportation Handbook: Maintaining Product Quality During Transportation, http://www.rockymountainbusiness.com/AgExporters/maintaining_product_quality.htm.
USDA. Tropical Products Transport Handbook. USDA [usda.gov/tmd/Tropica1] (2006).
U.S. Global Resources, Plant Growth 1 Germination Cabinets, www.usgr.com.
Van Doorn, "Does Ethylene Treatment Mimic the Effects of Pollination on Floral Lifespan and Attractiveness?" Annals of Botany 89:375-83 (2002).
Van Doorn, "Effect of Ethylene on Flower Abscission: a Survey" Annals of Botany 89:689-93 (2002).
Van Doorn, "Categories of petal senescence and abscission: a re-evaluation" Annals of Botany 87:447-56 (2001).
Wagstaff et al., "Ethylene and flower longevity in Alstroemeria: relationship between tepal senescence, abscission and ethylene biosynthesis" J. Exp. Botany. 56:1007-16 (2005).
Wang et al., "An in vivo experimental system to study sugar phloem unloading in ripening grape berries during water deficiency stress," Annals of Botany, 92:523-8 (2003).
Wang et al., "Ethylene biosynthesis and signaling networks," The Plant Cell, Supplement 2002, S131-S151 (2002).
Wang et al., "Regulation of ethylene gas biosynthesis by the *Arabidopsis* ETI protein" Nature. 428:945-50 (2004).
Watanabe et al., "Screening, Isolation and Taxonomical Properties of Microorganisms Having Acrylonitrile Hydrating Activity" Agric. Biol. Chem. 51:3193-9 (1987).

(56) References Cited

OTHER PUBLICATIONS

Watkins and Frenkel, "Inhibition of pear fruit ripening by mannose," Plant Physiol. 85:56-61 (1987).
Weingart and Volksch, "Ethylene production by Pseudomonas syringae pathovars in vitro and in planta." Appl. Environ. Microbiol. 63:156-161 (1997).
Whittaker et al., "Expression of ethylene biosynthetic genes in *Actinidia chinensis* fruit" Plant Malec. Biol. 343:45-55 (1997).
Wild, "Controlled atmosphere update: a cost benefit analysis—horses for courses," Intermodal 1998 Conference, Dec. 1-3, 1998, Rotterdam. www.drwild.de/I998-12-02_Intermodal_CA.pdf.
Wolf M, et al. "Stabilisation and determination of the biological activity of L-asparaginase in poly(D,L-lactide-co-glycolide) nanospheres." Int J Pharm. Apr. 30, 2003;256(1-2):141-52.
Woltering, "Interorgan translocation of 1-aminocyclopropane-1-carboxylic acid and ethylene coordinates senescence in emasculated Cymbidium flowers" Plant Physiol. 92:837-45 (1990).
Woodson et al., "Expression of ethylene biosynthetic pathway transcripts in senescing carnation flowers" Plant Physiol. 99:526-532 (1992).
Woodson and Lawton, "Ethylene-induced gene expression in carnation petals" Plant Physiol. 87:498-503 (1988).
Woolf et al., "I-MCP reduces physiological storage disorders of "Hass" avocados." Postharvest Biol. Technol. 35:43-60 (2005).
Worthington Enzyme Manual. Asparaginase. Worthington Biochemical Corporation. 2012.
Yamada et al., "Optimum culture conditions for production by Pseudomonas chloroaphis B23 of nitrile hydratase" Agric. Biol. Chem. 50(11):2859-65 (1986).
Yamaki, T., et al., "Closing and Sequencing of a Nitrile Hydratase Gene from *Pseudonocardia thermophile*, JCM3095," Journal of Fermentation and Bioengineering, vol. 83, No. 5, 1997, pp. 474-477.
Yang and Hoffman, "Ethylene biosynthesis and its regulationin higher plants" Ann. Rev. Plant Physiol. 35:155-89 (1984).
Zhao et al., "Elicitor signal transduction leading to production of plant secondary metabolites," Biotechnology Advances 23:283-333 (2005).
International Preliminary Report on Patentability, dated Jul. 31, 2012, received in connection with International Application No. PCT/US2011/022278.
International Search Report and Written Opinion, dated Oct. 14, 2011, received in connection with International Application No. PCT/US2011/022278.
International Search Report, dated Mar. 11, 2009, received in connection with International Application No. PCT/US2008/058286.
International Preliminary Report on Patentability, dated Aug. 20, 2009, received in connection with International Application No. PCT/US2008/058286.
International Search Report, dated Dec. 3, 2007, received in connection with International Application No. PCT/US2007/061315.
International Preliminary Report on Patentability, dated Jun. 25, 2008, received in connection with International Application No. PCT/US2007/061315.
International Search Report and Written Opinion of the International Searching Authority in PCT Application No. PCT/US2014/024491, dated Sep. 15, 2014, 11 pages.
International Search Report and Written Opinion for related International Application No. PCT/US2014/026371, dated Jul. 9, 2014.
Extended European Search Report in EP 11735319.3, dated Jul. 1, 2013.
Perry, Enhancing the Expression of Enzymes Used to Degrade Hydrocarbons and Cyanohydrins in Rhodococcus sp. DAP 96253 by Using Inducers such as Cobalt, Urea, and Propylene Gas; Also Enhances the Ability of the Bacteria to Delay the Ripening of Several Fruit Species, Biology Dissertations, Nov. 28, 2012.

* cited by examiner

A   B   C

PREVENTING OR DELAYING CHILL INJURY RESPONSE IN PLANTS

CROSS-REFERENCE TO RELATED APPLICATIONS

This application claims the benefit of U.S. Provisional Application No. 61/783,047, filed Mar. 14, 2013, which is hereby incorporated herein by reference in its entirety.

BACKGROUND

Chill injury in a plant causes a molecular response, which results in the production of plant signal compounds (ethylene, hydrogen cyanide (HCN), and carbon dioxide), which serve as part of a plant cascade system to cause the plant to exhibit a response upon exposure to colder temperatures. Examples of plants that exhibit a chill injury response include fruits, vegetables, and flowers.

The chill injury response can be negative in plants. In fruits and vegetables, the chill injury response can result in irreparable damage to the fruit or vegetable. The chill injury response in fruits and vegetables can produce undesirable results such as fermented flavor, fermented odor, discoloration, a water-soaked appearance, wilting, pitting, browning, softening, russeting, and rotting of the fruit or vegetable. The chill injury response in a flower can result in a darkening and water-soaked appearance; discoloration of the stem, sepals and petals; or wilting of the flower. Interference with the plant signaling systems causing the chill injury response can allow for increased and prolonged exposure to colder temperatures, which is critical for the transportation of fruits, vegetables, and flowers, as they are commonly refrigerated during shipment.

SUMMARY

Provided herein are methods for preventing or delaying a chill injury response of a plant or plant part that exhibits a chill injury response. The methods comprise exposing the plant or plant part to one or more bacteria, one or more enzymes, an enzymatic extract isolated from one or more bacteria, or any combination thereof, in a quantity sufficient to prevent or delay the chill injury response of the plant or plant part.

The details of one or more aspects are set forth in the accompanying drawings and description below. Other features, objects, and advantages will be apparent from the description and drawings and from the claims.

DETAILED DESCRIPTION

Figure 1:
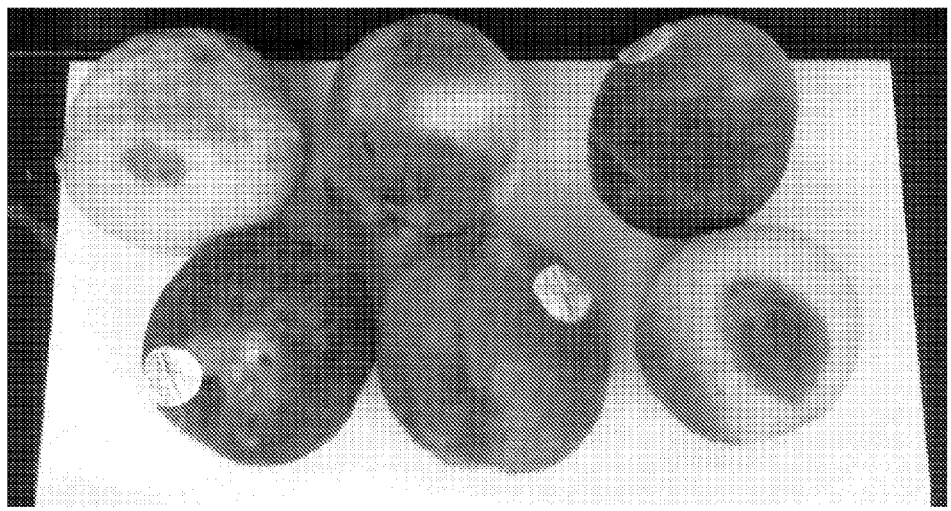
FIG. 1 shows an image of control peaches stored at 4° C. for 3 weeks.
Figure 2:
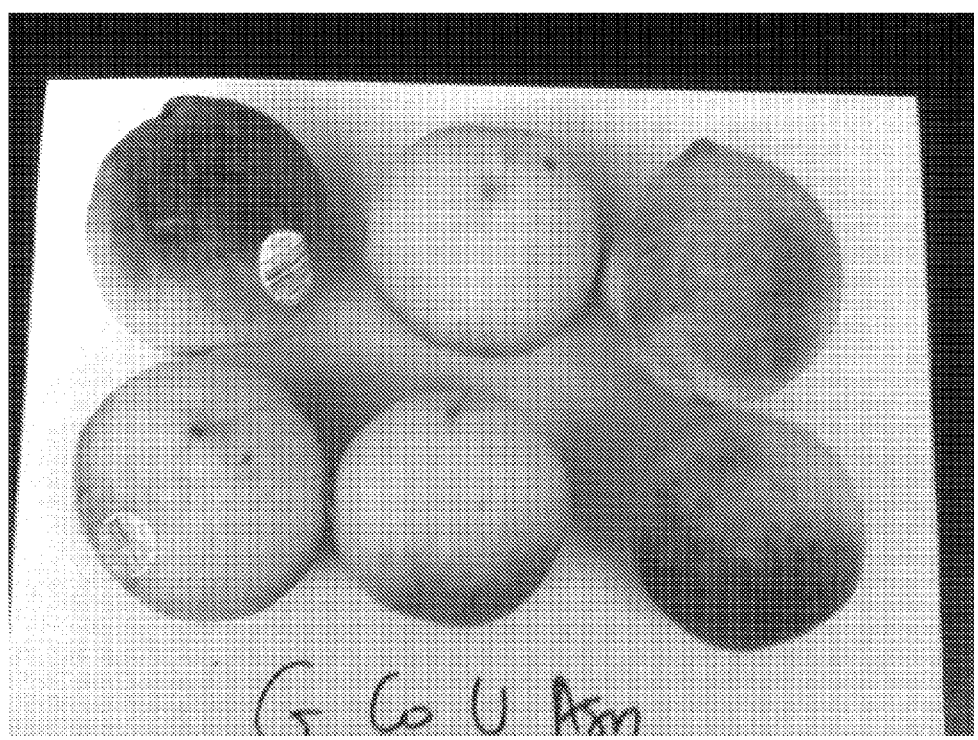
FIG. 2 shows an image of peaches stored at 4-7° C. for 3 weeks, and then exposed to the catalyst for 7 days, wherein the catalyst cells were grown on media with cobalt, urea, and asparagines.

As used herein, the singular forms "a," "an," and "the," include plural referents unless the context clearly dictates otherwise.

Throughout the specification, the term "comprising" and variations thereof are open, non-limiting terms and are understood to imply the inclusion of a stated element, integer or step, or group of elements, integers or steps, but not the exclusion of any other element, integer or step, or group of elements, integers or steps. The term "including" and variations thereof as used herein mean "comprising" and variations thereof.

Provided herein are methods and compositions for preventing or delaying a chill injury response of a plant or plant part that exhibits a chill injury response. The methods comprise exposing the plant or plant part to one or more bacteria, wherein the one or more bacteria are exposed to the plant or plant part in a quantity sufficient to prevent or delay the chill injury response of the plant or plant part. In some embodiments, the methods comprise exposing the plant or plant part to an enzymatic extract isolated from one or more bacteria, wherein the enzymatic extract is exposed to the plant or plant part in a quantity sufficient to prevent or delay the chill injury response of the plant or plant part. In some embodiments, the methods comprise exposing the plant or plant part to one or more enzymes as described herein, wherein the one or more enzymes are exposed to the plant or plant part in a quantity sufficient to prevent or delay the chill injury response of the plant or plant part. Optionally, the methods are carried out in a refrigerated device.

As used herein, "plant" or "plant part" is broadly defined to include intact plants and any part of a plant, including but not limited to fruit, vegetables, flowers, seeds, leaves, nuts, embryos, pollen, ovules, branches, kernels, ears, cobs, husks, stalks, roots, root tips, anthers, and the like. In particular embodiments, the plant part is a fruit, vegetable, or flower (including cut flowers). In certain aspects, the plant part is a fruit, vegetable, or flower.

The methods and compositions are drawn to preventing or delaying a chill injury response of a plant or plant part that exhibits a chill injury response. Chill injury response is generally associated with the production of plant signal compounds such as ethylene, HCN and carbon dioxide in the plant and is triggered by exposure of a plant to a temperature that is lower than the normal climatic temperature in which the plant grows, but not so low as to cause the cells of the plant or plant part to freeze. In some embodiments, the chill injury response is generally associated with increased ethylene biosynthesis. As defined herein, "preventing or delaying a chill injury response," and grammatical variants thereof, refers to any slowing, interruption, suppression, or inhibition of the chill injury response of a plant or plant part that exhibits the chill injury response. For example, preventing or delaying the chill injury response in a fruit or vegetable can comprise preventing or delaying a fermented flavor, a fermented odor, a discoloration, a water-soaked appearance, wilting, pitting, browning, softening, russeting, and/or rotting of the fruit or vegetable. By way of another example, preventing or delaying a chill injury response in a flower can comprise preventing or delaying a darkening and water-soaked appearance; a discoloration of the stem, sepals and petals; or wilting.

In certain embodiments, provided are methods and compositions for delaying a chill injury response in a fruit and/or a vegetable. A "fruit" or "vegetable" that exhibits a chill injury response can include, but is not limited to, apples, apricots, asparagus, avocados, bananas, beans, cantaloupe, cucumbers, eggplant, grapefruit, honeydew melons, lemons, lima beans, limes, mangos, nectarines, okra, oranges, papayas, peaches, peppers, pineapples, potatoes, pumpkins, soybeans, spinach, summer squash, sweet potatoes, tomatoes, watermelons, winter squash, and zucchini. In some embodiments, the fruit is a climacteric fruit. In some embodiments, the fruit is a non-climacteric fruit. Without intending to be limited by theory, while non-climacteric plants do not produce ethylene, the non-climacteric plants do respond to ethylene. Thus, when non-climacteric plants are exposed to cold, they can exhibit chill injury. Non-climacteric plants can be exposed to the one or more enzymes, enzymatic extract, or one or more bacteria to delay the chill injury response.

In certain embodiments, provided are methods and compositions for delaying a chill injury response in a flower. A "flower" that exhibits a chill injury response can include, but is not limited to, anthurium, basil, cattleyas, orchids, and poinsettias. In some embodiments, the methods and compositions are used to delay a chill injury response in an ornamental plant. Examples of ornamental plants include, but are not limited to, *Acacia*, *Achillea*, African Boxwood, African Lily, African Violet, *Agapanthus*, *Ageratum*, *Ageratum houstonim*, *Allium*, *Alpina*, *Alstroemeria*, *Amaranthus hypochondriacus*, *Amaryllis*, *Ammi majus*, *Anconitum*, *Anemone*, *Anigozanthus*, Annual *Delphinium*, *Anthurium*, *Antirrhinum majus*, Asparagus, *Aster* spp., *Astilbe*, Azalea, Baby's Breath, Bachelor's Button, *Banksia*, Begonia, Bellflower, Bells of Ireland, Big Flax, Billy Buttons, Blazing Star, Bleeding Heart, *Boronia*, *Bouvardia*, Broom, *Buddleia*, *Bupleurum*, Butterfly Bush, Butterfly Orchid, California Pepperberry, Calla Lily, Campanul, Candytuft, Canterbury Bells, Carnation, *Carthamus*, *Caspia*, *Cattleya*, *Celosia*, *Celosia argenta*, *Centaurea cyanus*, *Chamelaucium*, Chimney Bells, Chrysanthemum, Chrysanthemum×morifolium, *Clarkia*, *Consolida ambigua*, *Convallaria*, Coral Bell, Cordyline, *Coreopsis*, Cornflower, *Craspedia*, Curly Willow, *Cyclamen*, *Cymbidium*, *Cymbidium* Orchid, Daffodil, Daisy, Daisy Mums, Daylily, *Delphinium*, *Dendrobium*, *Dendrobium Orchid*, *Dianthus barbatus*, *Dianthus caryophyllus*, *Dianthus caryophyllus nana*, Dragon's Tongue, Drumstick, *Enthusiasm*, *Erica* spp, *Eustoma grandiflorum*, False Bird of Paradise, False Spirea, Farewell-To-Spring, Flamingo Flower, Floss Flower, *Freesia*, *Freesia×hybrida*, Fuji or spider Mums, Gay Feather, *Genista* spp., Geranium, *Gerbera*, *Gerbera* spp., Ginger, *Gladiolus*, *Gladiolus hybrid nanus*, Goat's Beard, *Godetia*, Golden Rod, Guersney Lily, Gyp, *Gypsophila paniculata*, Hanging Helicona, Heath, Heather, *Helianthus annuus*, *Heliconia* spp., *Hippeastrum*, *Hosta*, *Hydrangea*, *Iberis amara*, *Impatiens*, Inca Lily, *Iris*, *Iris* spp., Ivory Lily, Jade plant, Japhette Orchid, Jonquil, Kalanchoe, Kangaroo Paw, napweed, Larkspur, *Lathyrus odoratus*, *Lavandula*, Lavender, *Liatris*, Lilac, *Lilium* spp., Lily of-the Valley, Lily, Lily of the Field, Lily of the Nile, *Limonium*, *Limonium* spp., *Lisianthus*, Lobster Claw, Love in the mist, Love-lies-bleeding, *Mattholia incana*, Memosa, Minature Carnation, Mini Carnation, Miniature Gladiolus, *Moluccella laevis*, Monkshood, Mother-in-law tongue, *Musa*, Myrsine, Myrtle, *Myrtus*, *Narcissus*, *Nephrolepis*, Nerine, Nerine Lily, *Nigella*, Orchid, Ornamental Onion, Ornithogalum, Paeonia, Painted Tongue, Peony, Peruvian lily, *Petunia*, *Phalaenopsis*, *Philodendron*, *Phlox*, Pincushion Flower, Pitt, *Pittosporum*, Pixie Carnation, Pointsettia, *Polianthes tuberosa*, Pompon Chrysanthemum, Poppy Anemone, *Porium*, *Protea* spp., Purple Coneflower, Pussy Willow, Queen Ann's Lace, *Ranunculus*, Rattlesnake, Red Ribbons, *Rosa* spp., Rose, Rudbeckia, Safflower, *Salix*, *Salvia*, *Sansevieria*, Satin Flowers, *Scabiosa*, *Schinus*, Sea lavender, *Sedum*, Shell Flowers, Snake Plant, Snapdragon, *Solidago*, *Solidaster* spp., Speedwell, Spider Lily, Spider Mums, Spray Carnation, Star of Bethlehem, Statice, Stenamezon, Stock, Summer's Darling, Sunflower, Sweet Pea, Sweet William, Sword Fern, *Syringa vulgaris*, Tailflowers, Tassel flower, Thouroughwax, Throatwort, *Trachelium*, Tree Fern, Trumpet Lily, Tuberose, Tulip, *Tulipa*, *Veronica*, Wattle, Waxftower, Wild Plantain, Windflower, Wolfsbane, Youth and Old Age, *Zantedeschia*, *Zinna*, *Zinnia elegans*, and *Zygocactus*.

In certain embodiments, the methods and compositions for preventing or delaying a chill injury response in a plant comprises exposing the plant or plant part to one or more bacteria selected from the group consisting of *Rhodococcus* spp., *Brevibacterium ketoglutamicum*, *Pseudomonas chloroaphis*, *Nocardia*, *Pseudonocardia* and combinations thereof. The one or more bacteria can, for example, include *Rhodococcus* spp. The *Rhodococcus* spp can, for example, include *Rhodococcus rhodochrous* DAP 96253 strain, *Rhodococcus rhodochrous* DAP 96622 strain, *Rhodococcus erythropolis*, or combinations thereof. Exemplary organisms include, but are not limited to, *Pseudomonas chloroaphis* (ATCC 43051) (Gram-negative), *Pseudomonas chloroaphis* (ATCC 13985) (Gram-negative), *Rhodococcus erythropolis* (ATCC 47072) (Gram-positive), and *Brevibacterium ketoglutamicum* (ATCC 21533) (Gram-positive). Examples of *Nocardia* and *Pseudonocardia* species have been described in European Patent No. 0790310; Collins and Knowles J. Gen. Microbiol. 129:711-718 (1983); Harper Biochem. J. 165:309-319 (1977); Harper Int. J. Biochem. 17:677-683 (1985); Linton and Knowles J Gen. Microbiol. 132:1493-1501 (1986); and Yamaki et al., J. Ferm. Bioeng. 83:474-477 (1997).

Although in some embodiments the one or more bacteria are selected from the group consisting of *Rhodococcus* spp., *Brevibacterium ketoglutamicum*, and *Pseudomonas chloroaphis*, any bacterium that prevents or delays a chill injury response when exposed to a plant or plant part can be used in the present methods. For example, bacteria belonging to the genus *Nocardia* [see Japanese Patent Application No. 54-129190], *Rhodococcus* [see Japanese Patent Application No. 2-470], *Rhizobium* [see Japanese Patent Application No. 5-236977], *Klebsiella* [Japanese Patent Application No. 5-30982], *Aeromonas* [Japanese Patent Application No. 5-30983], *Agrobacterium* [Japanese Patent Application No. 8-154691], *Bacillus* [Japanese Patent Application No. 8-187092], *Pseudonocardia* [Japanese Patent Application No. 8-56684], *Burkholderia, Corynebacterium*, and *Pseudomonas* are non-limiting examples of bacteria that can be used. Not all species within a given genus exhibit the same type of enzyme activity and/or production. Thus, it is possible to have a genus generally known to include strains capable of exhibiting a desired activity but have one or more strains that do not naturally exhibit the desired activity or one or more strains which do not exhibit the activity when grown on the same medium as the species which exhibit this activity. Thus, host microorganisms can include strains of bacteria that are not specifically known to have the desired activity but are from a genus known to have specific strains capable of producing the desired activity. Such strains can have transferred thereto one or more genes useful to cause the desired activity. Non-limiting examples of such strains include *Rhodococcus equi* and *Rhododoccus globerulus* PWD1.

Further, specific examples of bacteria include, but are not limited to, *Nocardia* sp., *Rhodococcus* sp., *Rhodococcus rhodochrous, Klebsiella* sp., *Aeromonas* sp., *Citrobacter freundii, Agrobacterium rhizogenes, Agrobacterium tumefaciens, Xanthobacter flavas, Erwinia nigrifluens, Enterobacter* sp., *Streptomyces* sp., *Rhizobium* sp., *Rhizobium loti, Rhizobium legminosarum, Rhizobium merioti, Pantoea agglomerans, Klebsiella pneumoniae* subsp. *pneumoniae, Agrobacterium radiobacter, Bacillus smithii, Pseudonocardia thermophila, Pseudomonas chloroaphis, Rhodococcus erythropolis, Brevibacterium ketoglutamicum*, and *Pseudonocardia thermophila*. Optionally, the microorganisms used can, for example, comprise *Rhodococcus rhodochrous* DAP 96253 and *Rhodococcus rhodochrous* DAP 96622, and combinations thereof.

As used herein, exposing the plant or plant part to one or more bacteria includes, for example, exposure to intact bacterial cells, bacterial cell lysates, bacterial extracts that possess enzymatic activity (i.e., "enzymatic extracts"), or any combination thereof. Methods for preparing lysates and enzymatic extracts from cells, including bacterial cells, are routine in the art. Optionally, the one or more bacteria or enzymatic extracts are fixed with glutaraldehyde and cross-linked. Optionally, the crosslinked, glutaraldehyde-fixed bacteria or extract is formulated with a carrier into a spray.

In certain embodiments, the methods and compositions for preventing or delaying a chill injury response in a plant or plant part comprise exposing the plant or plant part to an enzyme. The enzyme can be selected from the group consisting of nitrile hydratase, amidase, asparaginase, ACC (1-aminocyclopropane-1-carboxylic acid) deaminase, cyanoalanine synthase-like enzyme, alkane monooxygenase, ammonium monooxygenase, methane monooxygenase, toluene dioxygenase, cyanidase, and/or a combination thereof. The enzyme can be provided within a composition for exposure to the plant or plant part. The enzyme can also be a purified enzyme or can be provided as an enzymatic extract as described above. Optionally, the methods for preventing or delaying a chill injury response in a plant or plant part comprise exposing the plant or plant part to a composition comprising an enzyme, the enzyme being selected from one or more of nitrile hydratase, amidase, asparaginase, ACC deaminase, cyanoalanine synthase-like enzyme, alkane monooxygenase, ammonium monooxygenase, methane monooxygenase, toluene dioxygenase, and cyanidase. The one or more bacteria, enzymatic extract, or enzymes used in the methods may at times be more generally referred to herein as the "catalyst."

In the methods provided herein, the plant or plant part are exposed to one or more bacteria, one or more enzymes, enzymatic extract isolated from or derived from the one or more bacteria, or any combination thereof, in a quantity sufficient to delay the chill injury response. In some embodiments, the plant or plant part is exposed to one or more bacteria in combination with one or more exogenous enzymes and/or enzymatic extracts. "Exogenous" refers to enzymes or enzymatic extracts that are isolated and/or purified ex situ and is distinguished from enzymes produced by bacteria in situ. This combined exposure can take place simultaneously and/or sequentially. For example, the plant can be exposed to exogenous enzymes and/or enzymatic extracts 1 to 60 minutes, 1 to 24 hours, or 1 to 7 days after exposure to the bacteria.

"Exposing" a plant or plant part to one or more bacteria, one or more enzymes, and/or an enzymatic extract includes any method of presenting a bacterium, enzyme, and/or extract to the plant or plant part. Optionally, the plant or plant part is indirectly exposed to the one or more bacteria, one or more enzymes, and/or the enzymatic extract. Indirect methods of exposure include, for example, placing the one or more bacteria, one or more enzymes, and/or enzymatic extract in the general proximity of the plant or plant part (i.e., indirect exposure). Optionally, the plant or plant part is directly exposed to one or more bacteria, one or more enzymes, and/or the enzymatic extract, whereby the one or more bacteria, one or more enzymes, and/or enzymatic extract are in direct contact with the plant or plant part.

In certain embodiments, exposure of the bacteria, enzyme, and/or the enzymatic extract isolated from the bacteria can occur, for example, by providing the bacteria, enzyme, and/or enzymatic extract in liquid form and spraying it onto or near the plant or plant part. The bacteria, enzyme, and/or enzymatic extract can, for example, further comprise a liquid carrier. Liquid carriers can be selected from the group consisting of an aromatic hydrocarbon, a substituted naphthalene, a phthalic acid ester, an aliphatic hydrocarbon, an alcohol, and a glycol. Optionally, the liquid carrier can be a wax or similar type material coating, which could be applied to the plant as a liquid, but would be solid at ambient or lower temperatures.

In certain embodiments, exposure of the one or more bacteria, one or more enzymes, and/or the enzymatic extract isolated from the bacteria can occur, for example, by providing the bacteria, enzyme, and/enzymatic extract in solid form and dusting it onto or near the plant or plant part. The bacteria, enzyme, and/or enzymatic extract can, for example, further comprise a solid carrier. The solid carrier can be selected from the group consisting of a dust, a wettable powder, a water dispersible granule, and mineral fillers. Optionally, the solid carrier is a mineral filler. Mineral fillers can, for example, be selected from the group consisting of a calcite, a silica, a talc, a kaolin, a montmorillonite, and an attapulgite. Other solid supports for use with the bacteria, enzyme, and/or enzymatic extract are described herein.

In certain embodiments, the one or more bacteria, one or more enzymes, and/or enzymatic extract further comprise a hydrophobic fatty acid polyester coating, wherein the hydrophobic fatty acid polyester coating makes the bacteria or enzymatic extract water resistant. Optionally, the hydrophobic fatty acid polyester coating is a long chain fatty acid polyester derived from sucrose, sorbitol, sorbinose, glycerol, or raffinose.

Also provided herein are compositions for preventing or delaying a chill injury response of a plant or plant part that exhibits a chill injury response. The compositions can, for example, comprise one or more bacteria, one or more enzymes, and/or one or more enzymatic extracts capable of delaying a chill injury response of a plant or plant part that exhibits a chill injury response. The compositions can further comprise solid, liquid, and gelatinous carriers, as disclosed above, and/or media and media components for inducing and stabilizing the one or more bacteria, one or more enzymes, and/or enzymatic extracts, as disclosed below.

The provided methods and compositions for preventing or delaying a chill injury response in a plant or plant part can be combined with other agents known to delay chill injury response. Thus, for example, the provided methods can further comprise exposing a plant or plant part to an agent that delays or prevents a chill injury response. Such agents include, for example, synthetic analogues of phytohormones. Likewise, the provided compositions can further comprise an agent that delays or prevents a chill injury response, such as a synthetic analogue of a phytohormone.

As defined herein, a "sufficient" quantity or effective amount of the bacteria, enzyme, and/or enzymatic extract will depend on a variety of factors, including, but not limited to, the particular bacteria, enzyme, and/or enzymatic extract used in the method, the form in which the bacteria is exposed to the plant or plant part (e.g., as intact bacterial cells (alive or dead), cell lysates, enzymatic extracts, or enzymes as described above), the means by which the bacteria, enzyme, and/or enzymatic extract is exposed to the plant or plant part, the length of time of the exposure, and the type and amount of plant signal compounds that produce the chill injury response. Optionally, the quantity of bacteria exposed to the plant or plant part is in the range of 1 to 250 mg of cell-dry weight (per pound of plant [i.e., fruit, etc.]) or the equivalent thereof for enzymatic extracts and enzymes. For 1 mg of dry weight of cells, typically there are 150-300 units of nitrile hydratase, 10-25 units of amidase, 7-15 units of cyanidase, 7-20 units of ACC deaminase, and 7-20 units of cyanoalanine synthase-like enzyme. By way of other examples, the quantity of bacteria exposed to the plant or plant part is in the range of 0.1 to 400 mg, 1 to 200 mg, 1 to 80 mg, or 1 to 10 mg of cell-dry weight or the equivalent thereof for enzymatic extracts and enzymes. Optionally, the quantity of bacteria exposed to the plant or plant part is 1-3 mg of cell-dry weight per kilogram of plant or plant part or the equivalent thereof for enzymatic extracts and enzymes. By way of other examples, the quantity of bacteria exposed to the plant or plant part is 10 µg-100 mg, 100 µg-50 mg, 100 µg-25 mg, or 1-10 mg of cell-dry weight per kilogram of plant or plant part or the equivalent thereof for enzymatic extracts and enzymes. It would be a matter of routine experimentation for the skilled artisan to determine the "sufficient" quantity of the one or more bacteria, one or more enzymes, or enzymatic extract necessary to delay a chill injury response in a plant or plant part that exhibits a chill injury response.

In certain embodiments, the one or more bacteria are "induced" to exhibit a desired characteristic (e.g., the ability to delay a chill injury response in a plant or plant part that exhibits a chill injury response, the expression of a desired level of activity of an enzyme of the bacteria, and/or the ability to reduce the level of ethylene and/or hydrogen cyanide produced by the plant) by exposure or treatment with a suitable inducing agent. Inducing agents include, but are not limited to urea, methyl carbamate, cobalt, asparagine, glutamine, and combinations thereof. Optionally, the one or more bacteria are exposed to or treated with urea or methyl carbamate. Optionally, the one or more bacteria are exposed to or treated with a mixture of inducing agents comprising urea or methyl carbamate and one or more of asparagine and cobalt. The inducing agent can be added at any time during cultivation of the desired cells. For example, with respect to bacteria, the culture medium can be supplemented with an inducing agent prior to beginning cultivation of the bacteria. Alternately, the bacteria could be cultivated on a medium for a predetermined amount of time to grow the bacteria and the inducing agent could be added at one or more predetermined times to induce the desired enzymatic activity in the bacteria. Moreover, the inducing agent could be added to the growth medium (or to a separate mixture including the previously grown bacteria) to induce the desired activity in the bacteria after the growth of the bacteria is completed or during a second growth or maintenance phase.

While not intending to be limited to a particular mechanism, "inducing" the bacteria may result in the production or activation (or increased production or increased activity) of one or more of enzymes, such as nitrile hydratase, amidase, asparaginase, ACC deaminase, cyanoalanine synthase-like enzyme, alkane monooxygenase, ammonium monooxygenase, methane monooxygenase, toluene dioxygenase, and/or cyanidase, and the induction of one or more of these enzymes may play a role in delaying a chill injury response in a plant or plant part. "Nitrile hydratases," "amidases," "asparaginases," "ACC deaminases," "cyanoalanine synthase-like enzymes," "AMO-type (alkane or ammonium) monooxygenases," "methane monooxygenases," "toluene dioxygenases," and "cyanidases" comprise families of enzymes present in cells from various organisms, including but not limited to, bacteria, fungi, plants, and animals. Such enzymes are well known, and each class of enzyme possesses recognized enzymatic activities.

The methods of inducing an enzymatic activity can be accomplished without the requirement of introducing hazardous nitriles, such as acrylonitrile, into the environment. Previously, it was believed that induction of specific enzyme activity in certain microorganisms required the addition of chemical inducers. For example, in the induction of nitrile hydratase activity in *Rhodococcus rhodochrous* and *Pseudomonas chloroaphis*, it was generally believed to be necessary to supplement with hazardous chemicals, such as acetonitrile, acrylonitrile, acrylamide, and the like. However, enzymatic activity in nitrile hydratase producing microorganisms can be induced with the use of non-hazardous media additives, such as amide containing amino acids and derivatives thereof, and, optionally stabilized with trehalose. Optionally, asparagine, glutamine, or combinations thereof, can be used as inducers. Methods of inducing and stabilizing enzymatic activity in microorganisms are described in U.S. Pat. No. 7,531,343 and U.S. Pat. No. 7,531,344, which are incorporated herein by reference.

The disclosed methods of inducing enzymatic activity provide for the production and stability of a number of enzymes using modified media, immobilization, and stabilization techniques, as described herein. For example, enzymatic activity can be induced and stabilized through use of media comprising amide-containing amino acids, or derivatives thereof, and, optionally stabilized by, trehalose. In some embodiments, the methods of induction and stabilization comprise culturing a nitrile hydratase producing microorganism in a medium comprising one or more amide containing amino acids or derivatives thereof, and, optionally, trehalose. Optionally, disclosed are methods for inducing nitrile-hydratase using a medium supplemented with amide containing amino acids or derivatives thereof, which preferably include asparagine, glutamine or a combination thereof. Optionally, disclosed are methods for inducing nitrile-hydratase using a nutritionally complete medium supplemented with only asparagine. Optionally, disclosed are methods for inducing nitrile-hydratase using a nutritionally complete medium supplemented with only glutamine. Optionally, disclosed are methods for stabilizing nitrile-hydratase using a nutritionally complete medium supplemented with only trehalose. More particularly, the methods of induction and stabilization comprise culturing the microorganism in the medium and optionally collecting the cultured microorganisms or enzymes produced by the microorganisms.

Induction and stabilization of enzymes can be achieved without the use of hazardous nitriles. However, while the induction methods eliminate the need for hazardous chemicals for enzyme activity induction, the use of such further inducers is not excluded. For example, one or more nitriles could be used to assist in specific activity development. Media supplemented with succinonitrile and cobalt can be useful for induction of enzymes, including, for example, nitrile hydratase, amidase, asparaginase I, ACC deaminase, cyanoalanine synthase-like enzyme, alkane monooxygenase, ammonium monoxygenase, methane monooxygenase, toluene dioxygenase, and cyanidase. However, the use of nitriles is not necessary for induction of enzyme activity. While the use of nitriles and other hazardous chemicals is certainly not preferred, optionally, such use is possible.

Stabilization of enzyme activity can be achieved through immobilization methods, such as affixation, entrapment, and cross-linking, thereby, extending the time during which enzyme activity can be used. Thus, in some embodiments, induction methods and methods of delaying a chill injury response further comprise at least partially immobilizing the microorganism. Stabilization can be provided by immobilizing the enzymes, enzymatic extracts, and/or microorganisms producing the enzymes or enzymatic extracts. For example, enzymes or enzymatic extracts harvested from the microorganisms or the induced microorganisms themselves can be immobilized to a substrate as a means to stabilize the induced activity. Optionally, the nitrile hydratase producing microorganisms are at least partially immobilized. Optionally, the enzymes or microorganisms are at least partially entrapped in or located on the surface of a substrate. This allows for presentation of an immobilized material with induced activity (e.g., a catalyst) in such a manner as to facilitate reaction of the catalyst with an intended material and recovery of a desired product while simultaneously retaining the catalyst in the reaction medium and in a reactive mode.

Any substrate generally useful for affixation of enzymes, enzymatic extracts, and/or microorganisms can be used. Optionally, the substrate comprises alginate or salts thereof. Alginate is a linear copolymer with homopolymeric blocks of (1-4)-linked β-D-mannuronate (M) and its C-5 epimer α-L-guluronate (G) residues, respectively, covalently linked together in different sequences or blocks. The monomers can appear in homopolymeric blocks of consecutive G-residues (G-blocks), consecutive M-residues (M-blocks), alternating M and G-residues (MG-blocks), or randomly organized blocks. Optionally, calcium alginate is used as the substrate. The calcium alginate can, for example, be cross-linked, such as with polyethylenimine, to form a hardened calcium alginate substrate. Further description of such immobilization techniques can be found in Bucke, "Cell Immobilization in Calcium Alginate," Methods in Enzymology, vol. 135, Part B (ed. K. Mosbach) pp. 175-189 (1987), which is incorporated herein by reference. The stabilization effect of immobilization using polyethylenimine cross-linked calcium alginate is discussed in U.S. patent application Ser. No. 11/695,377, filed Apr. 2, 2007, which is hereby incorporated by reference in its entirety.

Optionally, the substrate comprises an amide-containing polymer. Any polymer comprising one or more amide groups can be used. Optionally, the substrate comprises a polyacrylamide polymer.

Stabilization can further be achieved through cross-linking. For example induced microorganisms can be chemically cross-linked to form agglutinations of cells. Optionally, the induced microorganisms are cross-linked using glutaraldehyde. For example, microorganisms can be suspended in a mixture of de-ionized water and glutaraldehyde followed by addition of polyethylenimine until maximum flocculation is achieved. The cross-linked microorganisms (typically in the form of particles formed of a number of cells) can be harvested by simple filtration. Further description of such techniques is provided in Lopez-Gallego, et al., J. Biotechnol. 119:70-75 (2005), which is incorporated herein by reference. In certain embodiments, the cross-linking kills or inactivates the microorganism. Thus, optionally, the induced microorganisms used in the present methods are dead (killed) or inactivated, but are still capable of exhibiting catalyst activity.

Optionally, the microorganisms, enzymes, and/or enzymatic extracts can be encapsulated rather than allowed to remain in the classic Brownian motion. Such encapsulation facilitates collection, retention, and reuse of the microorganisms and generally comprises affixation of the microorganisms to a substrate. Such affixation can also facilitate stabilization of the microorganisms, enzymes, and/or enzymatic extracts as described above, or may be solely to facilitate ease of handling of the induced microorganisms, enzymes, or enzymatic extracts.

The microorganisms, enzymes, and/or enzymatic extracts can be immobilized by any method generally recognized for immobilization of microorganisms, enzymes, and/or enzymatic extracts such as sorption, electrostatic bonding, covalent bonding, and the like. Generally, the microorganisms, enzymes, and/or enzymatic extracts are immobilized or entrapped on a solid support which aids in the recovery of the microorganisms enzymes, or enzymatic extracts from a mixture or solution, such as a detoxification reaction mixture. Suitable solid supports include, but are not limited to granular activated carbon, compost, wood or wood products, (e.g., paper, wood chips, wood nuggets, shredded pallets or trees), bran (e.g., wheat bran), metal or metal oxide particles (e.g., alumina, ruthenium, iron oxide), ion exchange resins, DEAE cellulose, DEAE-SEPHADEX® polymer, waxes/coating materials (such as those used as a coating for fruits and vegetables and optionally including a microbial control agent such as a fungicide or an insecticide), ceramic beads, cross-linked polyacrylamide beads, cubes, prills, or other gel forms, alginate beads, κ-carrageenan cubes, as well as solid particles that can be recovered from the aqueous solutions due to inherent magnetic ability. The shape of the catalyst is variable (in that the desired dynamic properties of the particular entity are integrated with volume/surface area relationships that influence catalyst activity). Optionally, the induced microorganism is immobilized in alginate beads that have been cross-linked with polyethylenimine or is immobilized in a polyacrylamide-type polymer.

In some embodiments, the compositions and medium used in the induction and stabilization methods further comprise one or more amide containing amino acids or derivatives thereof. The amide containing amino acids can, for example, be selected from the group consisting of asparagine, glutamine, derivatives thereof, or combinations thereof. For example, the amide-containing amino acids may include natural forms of asparagines, anhydrous asparagine, asparagine monohydrate, natural forms of glutamine, anhydrous glutamine, and/or glutamine monohydrate, each in the form of the L-isomer or D-isomer.

The concentration of the amide containing amino acids or derivatives thereof in the medium can vary depending upon the desired end result of the culture. For example, a culture may be carried out for the purpose of producing microorganisms having a specific enzymatic activity. Optionally, a culture may be carried out for the purpose of forming and collecting a specific enzyme from the cultured microorganisms. Optionally, a culture may be carried out for the purpose of forming and collecting a plurality of enzymes having the same or different activities and functions.

The amount of the amide containing amino acids, or derivatives thereof, added to the growth medium or mixture can generally be up to 10,000 parts per million (ppm) (i.e., 1% by weight) based on the overall weight of the medium or mixture. The induction methods are particularly beneficial, however, in that enzyme activity can be induced through addition of even lesser amounts. Optionally, the one or more amide containing amino acids are present at a concentration of at least 50 ppm. By way of other examples, the concentration of the amide containing amino acids or derivatives thereof is in the range of 50 ppm to 5,000 ppm, 100 ppm to 3,000 ppm, 200 ppm to 2,000 ppm, 250 ppm to 1500 ppm, 500 ppm to 1250 ppm, or 500 ppm to 1000 ppm.

In some embodiments, the induction methods include the use of trehalose. The concentration of trehalose in the compositions or medium used in the induction methods can be at least 1 gram per liter (g/L). Optionally, the concentration of trehalose is in the range of 1 g/L to 50 g/L, or 1 g/L to 10 g/L. Optionally, the concentration of trehalose in the medium is at least 4 g/L.

The amide containing amino acids or derivatives thereof and/or trehalose are added to a nutritionally complete media. A suitable nutritionally complete medium generally is a growth medium that can supply a microorganism with the necessary nutrients required for its growth, which minimally includes a carbon and/or nitrogen source. One specific example is the commercially available R2A agar medium, which typically consists of agar, yeast extract, proteose peptone, casein hydrolysate, glucose, soluble starch, sodium pyruvate, dipotassium hydrogenphosphate, and magnesium sulfate. Another example of a nutritionally complete liquid medium is Yeast Extract Malt Extract Agar (YEMEA), which consists of glucose, malt extract, and yeast extract (but specifically excludes agar). Also, media of similar composition, but of vegetable origin can be used for the disclosed methods. Any nutritionally complete medium known in the art could be used for the disclosed methods, the above media being described for exemplary purposes only. Such nutritionally complete media can be included in the compositions described herein.

Optionally, the disclosed compositions and media can contain further additives. Typically, the other supplements or nutrients are those useful for assisting in greater cell growth, greater cell mass, or accelerated growth. For example, the compositions and media can comprise a carbohydrate source in addition to any carbohydrate source already present in the nutritionally complete medium.

As described above, most media typically contain some content of carbohydrate (e.g., glucose); however, it can be useful to include an additional carbohydrate source (e.g., maltose or less refined sugars, such as dextrose equivalents that would be polymers of dextrose, or any carbohydrate that supports growth of the cell and induction of the desired activity). The type of excess carbohydrate provided can depend upon the desired outcome of the culture. For example, the addition of carbohydrates, such as maltose or maltodextrin, has been found to provide improved induction of asparaginase I. Additionally, the addition of carbohydrates, such as maltose or maltodextrin, potentially improves stability of enzymatic activity (e.g., nitrile hydratase activity).

In some embodiments, the compositions and media further comprise cobalt. Cobalt or a salt thereof can be added to the mixture or media. For example, the addition of cobalt (e.g., cobalt chloride) to the media can be particularly useful for increasing the mass of the enzyme produced by the cultured microorganisms. Cobalt or a salt thereof can, for example, be added to the culture medium such that the cobalt concentration is an amount up to 400 ppm. Cobalt can, for example, be present at a concentration of 5 ppm to 400 ppm, 10 ppm to 100 ppm, 10 ppm to 80 ppm, or 10 ppm to 25 ppm.

In some embodiments, the compositions and media further comprise urea. Urea or a salt thereof can be added to the mixture or media. Urea or a salt thereof can, for example, be added to the culture medium such that the urea concentration is in an amount up to 10 g/L. Urea can, for example, be present in a concentration of 5 g/L to 30 g/L, 5 g/L to 20 g/L, 5 g/L to 12 g/L, or 7 g/L to 10 g/L. Optionally, urea is present at a concentration of 7.5 g/L. Optionally, both urea and cobalt are added to the media.

The compositions and media may also include further components. For example, other suitable medium components may include commercial additives, such as cottonseed protein, maltose, maltodextrin, and other commercial carbohydrates. Optionally, the medium further comprises maltose or maltodextrin. Maltose or maltodextrin, for example, can be added to the culture medium such that the maltose or maltodextrin concentration is at least 1 g/L. Optionally, the compositions and media are free of any nitrile containing compounds. Nitrile compounds were previously required in the culture medium to induce enzyme activity toward two or more nitrile compounds. The compositions described herein achieve this through the use of completely safe trehalose and/or amide containing amino acids or derivatives thereof; therefore, the medium can be free of any nitrile containing compounds.

"Enzymatic activity," as used herein, generally refers to the ability of an enzyme to act as a catalyst in a process, such as the conversion of one compound to another compound. Likewise, the desired activity referred to herein can include the activity of one or more enzymes being actively expressed by one or more microorganisms. In particular, nitrile hydratase catalyzes the hydrolysis of nitrile (or cyanohydrin) to the corresponding amide (or hydroxy acid). Amidase catalyzes the hydrolysis of an amide to the corresponding acid or hydroxy acid. Similarly, an asparaginase enzyme, such as asparaginase I, catalyzes the hydrolysis of asparagine to aspartic acid. ACC deaminase catalyzes the hydrolysis of 1-aminocyclopropane-1-carboxylate to ammonia and α-ketobutyrate. Cyanoalanine synthase catalyzes the formation of the non-protein amino acid cyanoalanine from cysteine and cyanide. Cyanidase catalyzes the hydrolysis of cyanide to ammonia and formate. Alkane or ammonium monooxygenase (AMO) and methane monooxygenase catalyzes the hydrolysis of ethylene to ethylene epoxide. Toluene dioxygenase can, for example, oxidize ethylene, and is known as an AMO-like enzyme. Ethylene degradation activity results in the degradation of produced ethylene. In degrading ethylene and/or HCN, the plant cannot respond to the ethylene in a normal manner (i.e., the cascade effects of ethylene signaling are diminished and the ability of the plant to respond to an ethylene signal is disrupted). In the case of chill injury, without intending to be limited by theory, the plant will respond to chill injury with a burst of ethylene, mimicking accelerated ripening/decay. By degrading the ethylene and/or HCN, the plant does not respond to the chill injury or temperature transient and normal ripening (i.e., ripening that is not accelerated) can be experienced upon return of the plant to an ambient temperature.

Activity can be referred to in terms of "units" per mass of enzyme or cells (typically based on the dry weight of the cells, e.g., units/mg cdw). A "unit" generally refers to the ability to convert a specific content of a compound to a different compound under a defined set of conditions as a function of time. Optionally, one "unit" of nitrile hydratase activity refers to the ability to convert 1 µmol of acrylonitrile to its corresponding amide per minute, per milligram of cells (dry weight) at a pH of 7.0 and a temperature of 30° C. Similarly, one unit of amidase activity refers to the ability to convert 1 µmol of acrylamide to its corresponding acid per minute, per milligram of cells (dry weight) at a pH of 7.0 and a temperature of 30° C. Further, one unit of asparaginase I activity refers to the ability to convert 1 µmol of asparagine to its corresponding acid per minute, per milligram of cells (dry weight) at a pH of 7.0 and a temperature of 30° C. Further, one unit of ACC deaminase activity refers to the ability to convert 1 µmol of 1-aminocyclopropane-1-carboxylate to ammonia and α-ketobutyrate per minute, per milligram of cells (dry weight) at a pH of 7.0 and a temperature of 30° C. Further, one unit of cyanoalanine synthase activity refers to the ability to convert 1 µmol of cysteine and cyanide to cyanoalanine per minute, per milligram of cells (dry weight) at a pH of 7.0 and a temperature of 30° C. Further, one unit of cyanidase activity refers to the ability to convert 1 µmol of cyanide to ammonia and formate per minute, per milligram of cells (dry weight) at a pH of 7.0 and a temperature of 30° C. Further, one unit of alkane or ammonium monooxygenase (AMO) or methane monooxygenase activity refers to the ability to convert 1 µmol of ethylene to ethylene epoxide. Further, one unit of toluene dioxygenase refers to the ability to convert 1 µmol of ethylene to ethylene epoxide. Assays for measuring nitrile hydratase activity, amidase activity, asparaginase activity, ACC deaminase activity, cyanoalanine synthase-like enzyme activity, alkane or ammonium monooxygenase (AMO) activity, methane monooxygenase activity, toluene dioxygenase (AMO-like) activity, and cyanidase activity are known in the art and include, for example, the detection of free ammonia. See, e.g., Fawcett and Scott, J. Clin. Pathol. 13:156-9 (1960).

Generally, any bacterial, fungal, plant, or animal cell capable of producing or being induced to produce nitrile hydratase, amidase, asparaginase, ACC deaminase activity, cyanoalanine synthase-like enzyme activity, alkane or ammonium monooxygenase (AMO) activity, methane monooxygenase activity, toluene dioxygenase activity, and cyanidase activity, or any combination thereof may be used herein. A nitrile hydratase, amidase, asparaginase, ACC deaminase, cyanoalanine synthase-like enzyme, alkane or ammonium monooxygenase, methane monooxygenase, toluene dioxygenase, and/or cyanidase may be produced constitutively in a cell from a particular organism (e.g., a bacterium, fungus, plant cell, or animal cell) or, alternatively, a cell may produce the desired enzyme or enzymes only following "induction" with a suitable inducing agent. "Constitutively" is intended to mean that at least one enzyme disclosed herein is continually produced or expressed in a particular cell type. Other cell types, however, may need to be "induced," as described above, to express nitrile hydratase, amidase, asparaginase, ACC deaminase, cyanoalanine synthase-like enzyme, alkane or ammonium monooxygenase, methane monooxygenase, toluene dioxygenase, and cyanidase at a sufficient quantity or enzymatic activity level to delay a plant development process of interest. That is, an enzyme disclosed herein may only be produced (or produced at sufficient levels) following exposure to or treatment with a suitable inducing agent. Such inducing agents are known and outlined above. For example, the one or more bacteria are treated with an inducing agent such as asparagine, glutamine, cobalt, urea, trehalose, or any mixture thereof, more particularly a mixture of asparagine, cobalt, and urea. Furthermore, as disclosed in U.S. Pat. Nos. 7,531,343 and 7,531,344, which are incorporated by reference in their entireties, entitled "Induction and Stabilization of Enzymatic Activity in Microorganisms," asparaginase I activity can be induced in *Rhodococcus rhodochrous* DAP 96622 (Gram-positive) or *Rhodococcus rhodochrous* DAP 96253 (Gram-positive), in medium supplemented with amide containing amino acids or derivatives thereof. Other strains of *Rhodococcus* can also preferentially be induced to exhibit asparaginase I enzymatic activity utilizing amide containing amino acids or derivatives thereof.

*P. chloroaphis* (ATCC Deposit No. 43051), which produces asparaginase I activity in the presence of asparagine and ACC deaminase, and *B. kletoglutamicum* (ATCC Deposit No. 21533), a Gram-positive bacterium that has also been shown to produce asparaginase activity, are also used in the disclosed methods. Fungal cells, such as those from the genus *Fusarium*, plant cells, and animal cells, that express a nitrile hydratase, amidase, and/or an asparaginase, may also be used herein, either as whole cells or as a source from which to isolate one or more of the above enzymes.

The nucleotide and amino acid sequences for several nitrile hydratases, amidases, and asparaginases from various organisms are disclosed in publicly available sequence databases. A non-limiting list of representative nitrile hydratases and aliphatic amidases known in the art is set forth in Tables 1 and 2 and in the sequence listing. The "protein score" referred to in Tables 1 and 2 provide an overview of percentage confidence intervals (% Confid. Interval) of the identification of the isolated proteins based on mass spectroscopy data.

TABLE 1

Amino Acid Sequence Information for Representative Nitrile Hydratases

| Source organism | Accession No. | Sequence Identifier | Protein Score (% Confid. Interval) |
|---|---|---|---|
| Rhodococcus sp. | 806580 | SEQ ID NO: 1 | 100% |
| Nocardia sp. | 27261874 | SEQ ID NO: 2 | 100% |
| Rhodococcus rhodochrous | 49058 | SEQ ID NO: 3 | 100% |
| Uncultured bacterium (BD2); beta-subunit of nitrile hydratase | 27657379 | SEQ ID NO: 4 | 100% |
| Rhodococcus sp. | 806581 | SEQ ID NO: 5 | 100% |
| Rhodococcus rhodochrous | 581528 | SEQ ID NO: 6 | 100% |
| Uncultured bacterium (SP1); alpha-subunit of nitrile hydratase | 7657369 | SEQ ID NO: 7 | 100% |

TABLE 2

Amino Acid Sequence Information for Representative Aliphatic Amidases

| Source organism | Accession No. | Sequence Identifier | Protein Score (% Confid. Interval) |
|---|---|---|---|
| Rhodococcus rhodochrous | 62461692 | SEQ ID NO: 8 | 100% |
| Nocardia farcinica IFM 10152 | 54022723 | SEQ ID NO: 9 | 100% |
| Pseudomonas aeruginosa PAO1 | 15598562 | SEQ ID NO: 10 | 98.3% |
| Helicobacter pylori J99 | 15611349 | SEQ ID NO: 11 | 99.6% |
| Helicobacter pylori 26695 | 2313392 | SEQ ID NO: 12 | 97.7% |
| Pseudomonas aeruginosa | 150980 | SEQ ID NO: 13 | 94% |

Optionally, host cells that have been genetically engineered to express a nitrile hydratase, amidase, asparaginase, ACC deaminase, cyanoalanine synthase-like enzyme, alkane monooxygenase, toluene dioxygenase, and/or cyanidase can be exposed to a plant or plant part for preventing or delaying a chill injury response. Specifically, a polynucleotide that encodes a nitrile hydratase, amidase, asparaginase, ACC deaminase, cyanoalanine synthase-like enzyme, alkane or ammonium monooxygenase, methane monooxygenase, toluene dioxygenase, or cyanidase (or multiple polynucleotides each of which encodes a nitrile hydratase, amidase, asparaginase, ACC deaminase, cyanoalanine synthase-like enzyme, alkane or ammonium monooxygenase, methane monooxygenase, toluene dioxygenase, or cyanidase) may be introduced by standard molecular biology techniques into a host cell to produce a transgenic cell that expresses one or more of the enzymes. The use of the terms "polynucleotide," "polynucleotide construct," "nucleotide," or "nucleotide construct" is not intended to limit to polynucleotides or nucleotides comprising DNA. Those of ordinary skill in the art will recognize that polynucleotides and nucleotides can comprise ribonucleotides and combinations of ribonucleotides and deoxyribonucleotides. Such deoxyribonucleotides and ribonucleotides include both naturally occurring molecules and synthetic analogues. The polynucleotides described herein encompass all forms of sequences including, but not limited to, single-stranded forms, double-stranded forms, and the like.

Variants and fragments of polynucleotides that encode polypeptides that retain the desired enzymatic activity (i.e., nitrile hydratase, amidase, asparaginase, ACC deaminase, cyanoalanine synthase-like enzyme, alkane or ammonium monooxygenase, methane monooxygenase, toluene dioxygenase, or cyanidase activity) may also be used herein. By "fragment" is intended a portion of the polynucleotide and hence also encodes a portion of the corresponding protein. Polynucleotides that are fragments of an enzyme nucleotide sequence generally comprise at least 10, 15, 20, 50, 75, 100, 150, 200, 250, 300, 350, 400, 450, 500, 550, 600, 650, 700, 800, 900, 1,000, 1,100, 1,200, 1,300, or 1,400 contiguous nucleotides, or up to the number of nucleotides present in a full-length enzyme polynucleotide sequence. A polynucleotide fragment will encode a polypeptide with a desired enzymatic activity and will generally encode at least 15, 25, 30, 50, 100, 150, 200, or 250 contiguous amino acids, or up to the total number of amino acids present in a full-length enzyme amino acid sequence. "Variant" is intended to mean substantially similar sequences. Generally, variants of a particular enzyme sequence will have at least 40%, 45%, 50%, 55%, 60%, 65%, 70%, 75%, 80%, 85%, 90%, 91%, 92%, 93%, 94%, 95%, 96%, 97%, 98%, 99% or more sequence identity to the reference enzyme sequence, as determined by standard sequence alignment programs. Variant polynucleotides described herein will encode polypeptides with the desired enzyme activity. By way of example, the relatedness between two polynucleotides or two polypeptides can be described as identity. The identity between two sequences can be determined using the Needleman-Wunsch algorithm (Needleman and Wunsch, 1970, *J. Mol. Biol.* 48:443-453) as implemented in the Needle program of the EMBOSS package (EMBOSS: The European Molecular Biology Open Software Suite, Rice et al., 2000, *Trends Genet.* 16:276-7). The output of Needle labeled "longest identity" is used as the percent identity and is calculated as (Identical Residues (i.e., nucleotides or peptides)×100)/(Length of Alignment−Total Number of Gaps in Alignment).

As used in the context of production of transgenic cells, the term "introducing" is intended to mean presenting to a host cell, particularly a microorganism such as *Escherichia coli*, with a polynucleotide that encodes a nitrile hydratase, amidase, asparaginase, ACC deaminase, cyanoalanine synthase-like enzyme, alkane or ammonium monooxygenase, methane monooxygenase, toluene dioxygenase, and/or cyanidase. Optionally, the polynucleotide will be presented in such a manner that the sequence gains access to the interior of a host cell, including its potential insertion into the genome of the host cell. The disclosed methods do not depend on a particular protocol for introducing a sequence into a host cell, only that the polynucleotide gains access to the interior of at least one host cell. Methods for introducing polynucleotides into host cells are well known, including, but not limited to, stable transfection methods, transient transfection methods, and virus-mediated methods. "Stable transfection" is intended to mean that the polynucleotide construct introduced into a host cell integrates into the genome of the host and is capable of being inherited by the progeny thereof "Transient transfection" or "transient expression" is intended to mean that a polynucleotide is introduced into the host cell but does not integrate into the host's genome.

Furthermore, the nitrile hydratase, amidase, asparaginase, ACC deaminase, cyanoalanine synthase-like enzyme, alkane or ammonium monooxygenase, methane monooxygenase, toluene dioxygenase, or cyanidase nucleotide sequence may be contained in, for example, a plasmid for introduction into the host cell. Typical plasmids of interest include vectors having defined cloning sites, origins of replication, and selectable markers. The plasmid may further include transcription and translation initiation sequences and transcription and translation terminators. Plasmids can also include generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or optimally both. For general descriptions of cloning, packaging, and expression systems and methods, see Giliman and Smith, Gene 8:81-97 (1979); Roberts et al., *Nature* 328:731-734 (1987); Berger and Kimmel, Guide to Molecular Cloning Techniques, Methods in Enzymology, Vol. 152 (Academic Press, Inc., San Diego, Calif.) (1989); Sambrook et al., Molecular Cloning: A Laboratory Manual, Vols. 1-3 (2d ed; Cold Spring Harbor Laboratory Press, Plainview, N.Y.) (1989); and Ausubel et al., Current Protocols in Molecular Biology, Current Protocols (Greene Publishing Associates, Inc., and John Wiley & Sons, Inc., New York; 1994 Supplement) (1994). Transgenic host cells that express one or more of the enzymes may be used in the disclosed methods as whole cells or as a biological source from which one or more enzymes can be isolated.

Apparatuses and carriers for preventing or delaying a chill injury response and for performing the methods disclosed are further provided. In particular embodiments, an apparatus or carrier for preventing or delaying a chill injury response comprising a catalyst that comprises one or more bacteria selected from the group consisting of *Rhodococcus* spp., *Pseudomonas chloroaphis, Brevibacterium ketoglutamicum*, and mixtures thereof is disclosed herein. *Rhodococcus rhodochrous* DAP 96253 strain, *Rhodococcus rhodochrous* DAP 96622 strain, *Rhodococcus erythropolis*, or mixtures thereof may be used in certain aspects. The one or more bacteria of an apparatus or carrier are provided in a quantity sufficient to prevent or delay a chill injury response, as defined herein above. In other aspects, the catalyst comprises one or more enzymes (i.e., nitrile hydratase, amidase, asparaginase, ACC deaminase, cyanoalanine synthase-like enzyme, alkane or ammonium monooxygenase, methane monooxygenase, toluene dioxygenase, and/or cyanidase) in a quantity or at an enzymatic activity level sufficient to prevent or delay a chill injury response. Sources of the desired enzymes for use as a catalyst in the apparatuses or carriers disclosed herein are also described in detail above. For example, the catalyst may be used in the form of whole cells that produce (or are induced or genetically modified to produce) one or more of the enzymes disclosed herein or may comprise the enzyme(s) themselves in an isolated, purified, or semi-purified form. Optionally, the apparatus or carrier administers a sufficient quantity or effective amount of the catalyst in a refrigerated device to prevent or delay the chill injury response in the plant or plant part.

A carrier for compositions for preventing or delaying a chill injury response can, for example, be selected from the group consisting of paper, DEAC, cellulose, waxes, gluteraldehyde, and granular activated carbon. By way of an example, the catalyst can be incorporated into/on a paper or plastic label (e.g., sticker) that is placed on a fruit and adhered to the fruit for preventing or delaying a chill injury response. The sticker can include an adhesive layer having a surface that adheres to the fruit and a paper layer that includes the catalyst and that adheres to the surface opposing the surface that adheres to the fruit. The sticker can be provided on a backing layer. The sticker can be designed to release the catalyst in a continuous (e.g., a constant release) or non-continuous fashion (e.g., a release at a first time point followed by a release at a second time point, etc.). Optionally, the sticker can be designed to change colors upon release of the catalyst. Optionally, the sticker can be designed to determine injury of the fruit or vegetable based on the color of the sticker. By way of an example, the sticker could change color (e.g., yellow to green) when the fruit or vegetable has obtained injury, as determined by the ability of the catalyst to determine or assess the fruit or vegetable quality. The sticker is advantageous in that the sticker can be removed prior to consumption of the fruit or vegetable, which precludes the consumer from ingesting the catalyst and eliminates the need to wash off the catalyst. Additionally, the sticker provides for a defined catalyst loading on the fruit or vegetable. By way of another example, the catalyst is incorporated into an edible wax that can be coated on the desired product. By way of another example, the catalyst can be incorporated into a post harvest protection additive (e.g., a pesticide). By way of another example, the catalyst can be incorporated into a material (e.g., tissue paper, plastic cup or other packaging) designed to hold the fruit or vegetable, such that the fruit or vegetable is nested within the catalyst-infused material.

Apparatuses for preventing or delaying a chill injury response disclosed herein may be provided in a variety of suitable formats and may be appropriate for single use or multiple uses (e.g., "re-chargeable"). Furthermore, the apparatuses or carriers disclosed herein find use in both residential and commercial settings. For example, such apparatuses or carriers can be integrated into residential or commercial refrigerators, included in trains, trucks, etc., for long-distance transport of fruit, vegetables, or flowers, or used as stand-alone cabinets for the storage or transport of such plant products. Exemplary, non-limiting apparatuses are described herein below and depicted in FIGS. 5-8.

In particular embodiments, the catalyst is provided in an immobilized format. Any process or matrix for immobilizing the catalyst may be used so long as the ability of the one or more bacteria (or enzymes) to delay or accelerate a plant development process is retained. For example, the catalyst may be immobilized in a matrix comprising alginate (e.g., calcium alginate), carrageenan, DEAE-cellulose, or polyacrylamide. Other such matrices are well known in the art and may be further cross-linked with any appropriate cross-linking agent, including but not limited to glutaraldehyde and/or polyethylenimine, to increase the mechanical strength of the catalyst matrix. In one aspect, the catalyst is immobilized in a glutaraldehyde cross-linked DEAE-cellulose matrix. The catalyst, particularly the catalyst in an immobilized form, may be further presented as a "catalyst module element." A catalyst module element comprises a catalyst, such as an immobilized catalyst, within an additional structure that, for example, reduces potential contact with the catalyst, facilitates replacement of the catalyst, or permits air flow across the catalyst.

In one embodiment, the matrix comprises alginate, or salts thereof. Alginate is a linear copolymer with homopolymeric blocks of (1-4)-linked β-D-mannuronate (M) and its C-5 epimer α-L-guluronate (G) residues, respectively, covalently linked together in different sequences or blocks. The monomers can appear in homopolymeric blocks of consecutive G-residues (G-blocks), consecutive M-residues (M-blocks), alternating M and G-residues (MG-blocks), or randomly organized blocks. In one embodiment, calcium alginate is used as the substrate, more particularly calcium alginate that has been cross-linked, such as with polyethylenimine, to form a hardened calcium alginate substrate.

Further description of such immobilization techniques can be found in Bucke (1987) "Cell Immobilization in Calcium Alginate" in *Methods in Enzymology*, Vol. 135(B) (Academic Press, Inc., San Diego, Calif.; Mosbach, ed.), which is incorporated herein by reference. An exemplary method of immobilization using polyethylenimine cross-linked calcium alginate is also described below in Example 5. In another embodiment, the matrix comprises an amide-containing polymer. Any polymer comprising one or more amide groups could be used. In one embodiment, the substrate comprises a polyacrylamide polymer.

Increased mechanical strength of an immobilized catalyst matrix can be achieved through cross-linking. For example, cells can be chemically cross-linked to form agglutinations of cells. In one embodiment, cells harvested are cross-linked using glutaraldehyde. For example, cells can be suspended in a mixture of de-ionized water and glutaraldehyde followed by addition of polyethylenimine until maximum flocculation is achieved. The cross-linked cells (typically in the form of particles formed of a number of cells) can be harvested by simple filtration. Further description of such techniques is provided in Lopez-Gallego et al. (2005) *J. Biotechnol.* 119:70-75, which is hereby incorporated by reference in its entirety.

In certain aspects, the immobilized catalyst or one or more catalyst module elements are placed in, placed on, or affixed to a "physical structure." The physical structure includes but is not limited to a film, sheet, coating layer, box, pouch, bag, or slotted chamber capable of holding one or more catalyst module elements. In certain embodiments, the physical structure comprises a container suitable for transport or storage of fruit, vegetables, or flowers. The physical structure may further comprise more than one individual structure, whereby all of the individual structures are connected to a central catalyst or catalyst module element. A physical structure described herein above may optionally be refrigerated by external means or comprise a refrigeration unit within the physical structure itself.

Elements for monitoring the efficacy of the catalyst for preventing or delaying a chill injury response (e.g., to assess when the catalyst or catalyst module should be replaced) or for measuring or controlling air flow, moisture content/humidity, and carbon dioxide levels may be optionally included in an apparatus disclosed herein. Any apparatus for preventing or delaying a chill injury response may further comprise one or more elements to permit air flow to or through the catalyst or catalyst module element. The skilled artisan would readily envision other possible modifications to the apparatuses described herein for monitoring and controlling the atmospheric conditions (e.g., air flow, humidity, and carbon dioxide levels) of the catalyst, the catalyst module element, or the physical structure. Conditions such as temperature, atmospheric composition (e.g., relative humidity, $O_2$ and $CO_2$ levels, physical stress, light, chemical stress, radiation, water stress, growth regulators, and pathogen attack play an important role in respiration rates and significantly impact shelf-life of fruits, vegetables, flowers, and other plant-related products. Although temperature and atmospheric conditions for storage vary depending on the fruit, vegetable, or other plant product of interest, recommended storage temperatures are typically in the range of about 0° to about 20° C. with $O_2$ and $CO_2$ levels in the approximate ranges of 1-10% and 0-20%, respectively. A relative humidity of about 50% to about 100%, particularly 85% to about 95%, more particularly about 90% to about 95% is generally recommended for the storage of fruits, vegetables, and related plant products. Given the significant correlation between respiration rate and shelf-life of plant products, control of the above factors is important to delaying the deterioration of such products. Accordingly, a carbon dioxide scavenger can be provided in the apparatus to reduce the carbon dioxide content.

Figure 5:
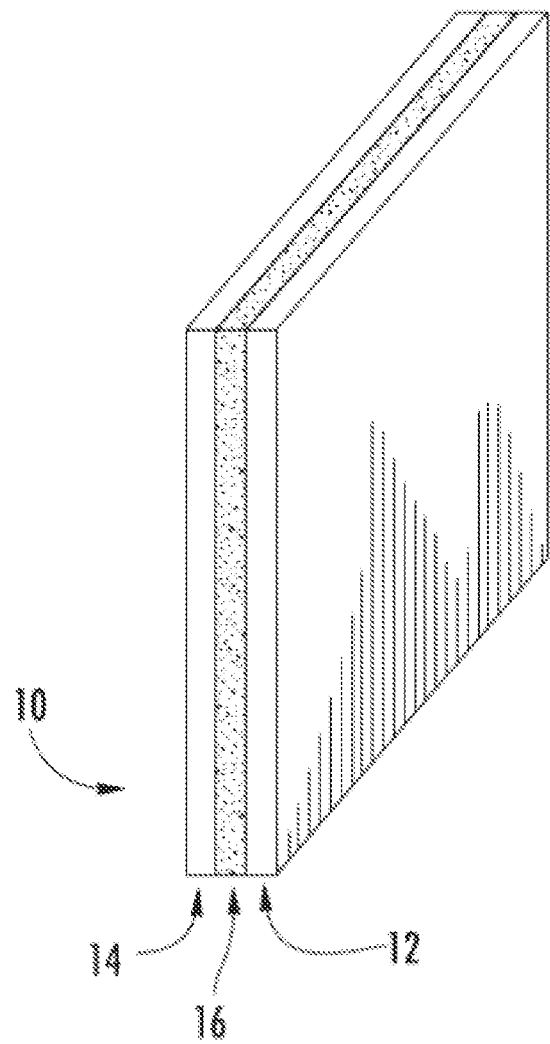
FIG. 5 shows a non-limiting depiction of a three-layer apparatus for preventing or delaying chill injury. The outer layers provide structural integrity to the apparatus. The catalyst layer, as defined herein below, comprises one or more of the disclosed enzymes and is located between the outer layers.

In particular embodiments, air-permeable catalyst apparatuses for preventing or delaying a chill injury response comprising multiple layers are provided. For example, as shown in FIG. 5, a catalyst apparatus 10 can include outer layers 12 and 14 and an intermediate catalyst layer 16 located between the outer layers 12 and 14. The catalyst layer 16 comprises one or more bacteria (e.g., *Rhodococcus* spp., *Pseudomonas chloroaphis, Brevibacterium ketoglutamicum*, and mixtures thereof) or enzymes (a nitrile hydratase, amidase, asparaginase, ACC deaminase, cyanoalanine synthase-like enzyme, alkane or ammonium monooxygenase, methane monooxygenase, toluene dioxygenase, cyanidase, and mixtures thereof), wherein the one or more bacteria or enzymes are provided in a quantity sufficient to prevent or delay a chill injury response, and a third layer. In this embodiment, one or more of the outer layers 12 and 14 provide structural integrity to the catalyst apparatus 10. The outer layers 12 and 14 typically permit air flow to the catalyst layer 16 although, in some embodiments, it may be advantageous to have an outer layer that is not air-permeable, e.g., if apparatus forms the side of the box and there is a desire not to allow the outermost layer of the box to expose the catalyst layer to the environment. The catalyst apparatus 10 can be provided in reusable or non-reusable bags or pouches. In one embodiment, the catalyst layer 16 comprises *Rhodococcus* spp. cells, particularly *Rhodococcus rhodochrous* DAP 96253 strain, *Rhodococcus rhodochrous* DAP 96622 strain, *Rhodococcus erythropolis*, or mixtures thereof. Bacterial cells utilized as a catalyst in an apparatus disclosed herein may be induced with one or more inducing agents (e.g., asparagine, glutamine, cobalt, urea, or a mixture thereof), as described in detail above.

Figure 6:
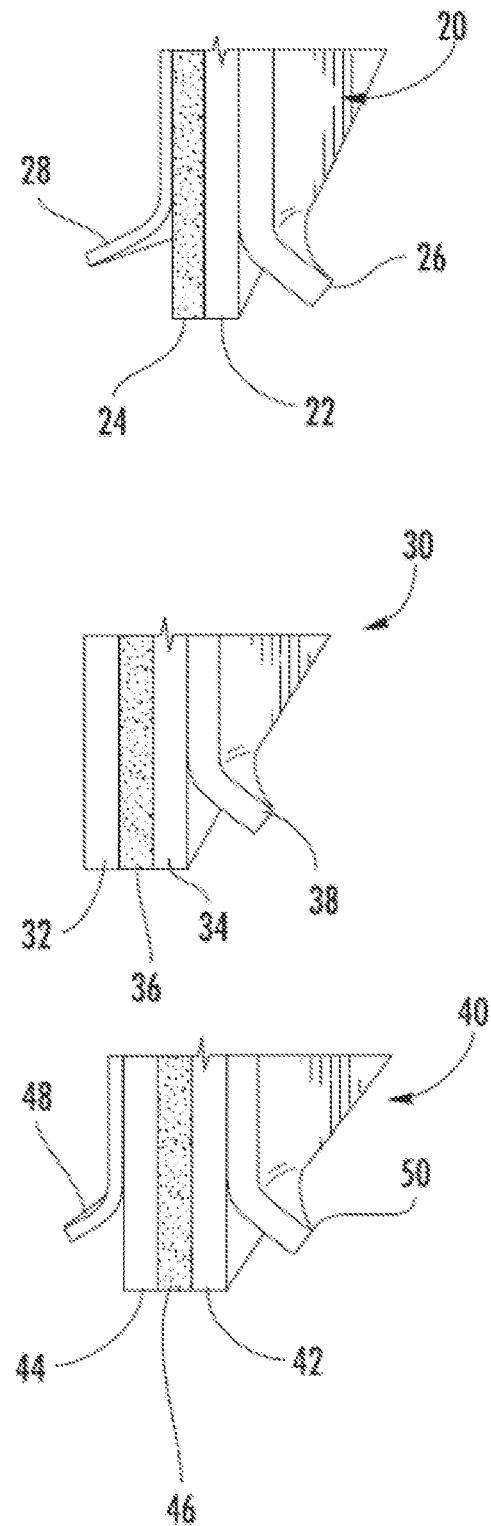
FIG. 6 provides non-limiting depictions of various apparatuses for preventing or delaying chill injury. These apparatuses comprise a catalyst layer, one or more layers intended to provide structural integrity, and one or more layers intended to be removed prior to use of the apparatus. Removal of one or more of these layers may, for example, expose an adhesive for attachment of the apparatus to another physical structure.

FIG. 6 illustrates alternative apparatuses for preventing or delaying a chill injury response. These apparatuses comprise multiple layers, wherein one or more of the layers are removable. As shown in FIG. 6, top diagram, the apparatus can include an air-permeable structural layer 22 and a catalyst layer 24. Removable layers 26 and/or 28 can be provided along the structural layer 22 and/or the catalyst layer 24 and are typically intended to be removed prior to using or activating the catalyst. In certain aspects, the removal of the removable layers 26 and 28 expose an adhesive that facilitates placement or attachment of the catalyst structure to a separate physical structure. FIG. 6, middle diagram, illustrates an alternative embodiment wherein the apparatus 30 includes two air-permeable structural layers 32 and 34, an intermediate catalyst layer 36 and a removable layer 38. FIG. 6, bottom diagram, illustrates yet another embodiment wherein the apparatus 40 includes two air-permeable structural layers 42 and 44, an intermediate catalyst layer 46 and two removable layers 48 and 50.

Figure 7:
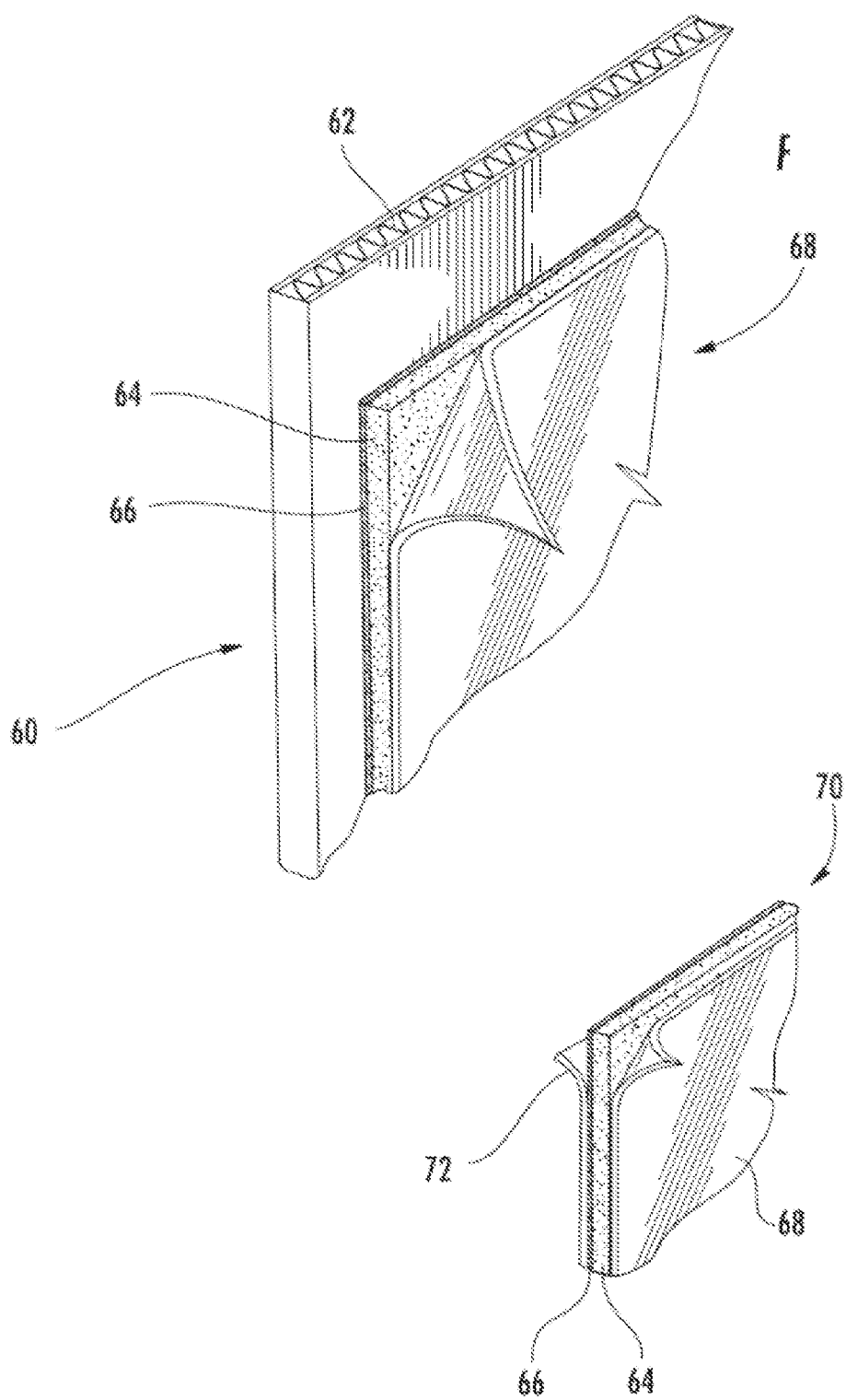
FIG. 7 shows a non-limiting depiction of an apparatus for preventing or delaying chill injury. The apparatus comprises a catalyst immobilized on a layer of film and attached to a physical structure (e.g., a box suitable for storage/transportation of fruit).

FIG. 7 illustrates an alternative embodiment 60 wherein the catalyst is affixed to the interior of a container such as a cardboard box. As shown in FIG. 7, top diagram, a side 62 of the container includes a catalyst layer 64 attached thereto through the use of an adhesive layer 66. A peelable film 68 can be provided adjacent the catalyst layer 64 to protect the catalyst layer from exposure to the environment. The peelable film 68 can be removed to activate the catalyst in the catalyst layer 64 by exposing the catalyst to a plant part provided in the container to thereby prevent or delay an undesired chill injury response.

Figure 3:
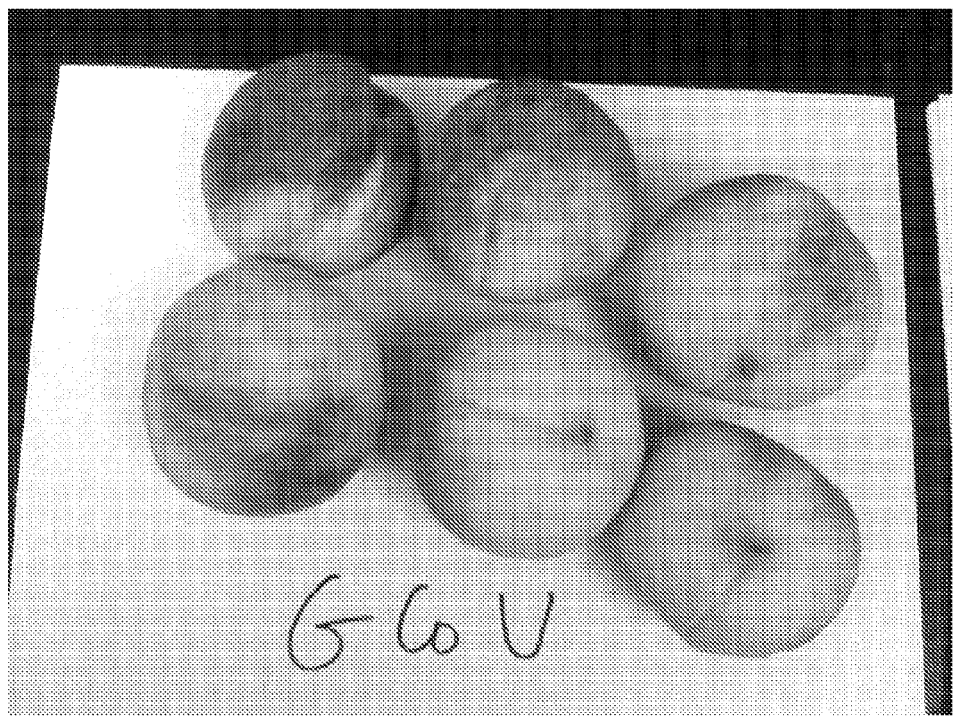
FIG. 3 shows an image of peaches stored at 4-7° C. for 3 weeks, and then exposed to the catalyst for 7 days, wherein the catalyst cells were grown on media with cobalt and urea.
Figure 4:
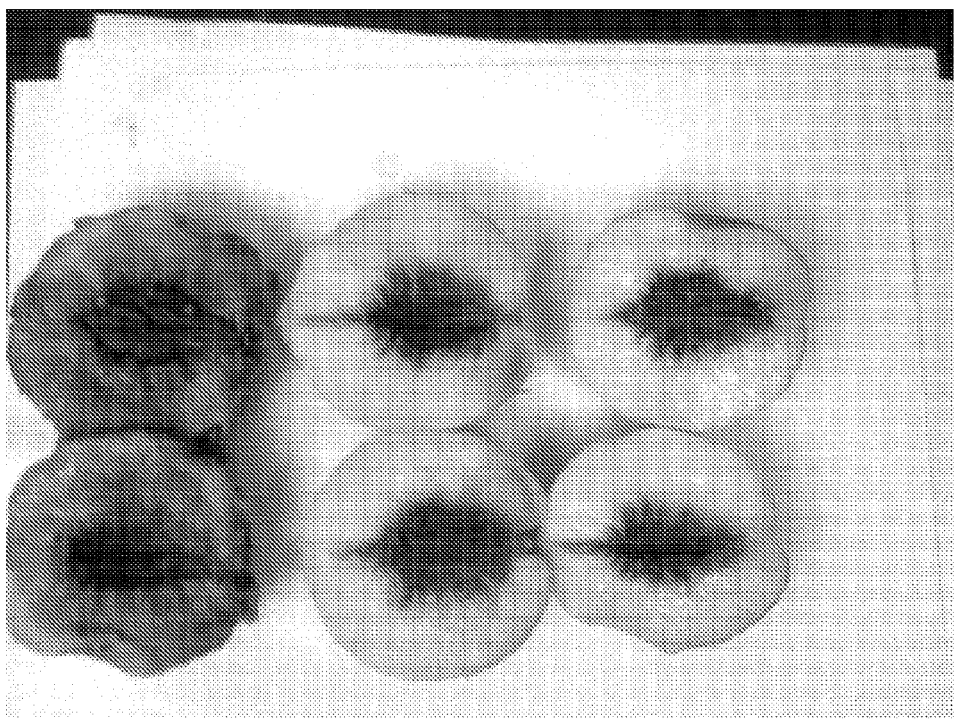
FIG. 4A shows an image of control peaches stored at 4-7° C. for 3 weeks.
FIG. 4B shows an image of peaches stored at 4-7° C. for 3 weeks and then exposed to the catalyst, wherein the catalyst cells were induced with cobalt and urea.
FIG. 4C shows an image of peaches stored at 4-7° C. for 3 weeks and then exposed to the catalyst, wherein the catalyst cells were induced with cobalt, urea, and asparagines.

FIG. 7, bottom diagram, illustrates a catalyst structure 70 prior to affixing the catalyst structure to a container interior in the manner shown in FIG. 7, bottom diagram. In addition to the catalyst layer 64, the adhesive layer 66, and the peelable film 68, the catalyst structure 70 includes an additional peelable film 72. The peelable film 72, like the peelable film 68, protects the catalyst structure 70 when it is packaged, shipped or stored. The peelable film 72 can be removed to expose the adhesive layer 66 to allow the catalyst structure 70 to be affixed to the container interior in the manner illustrated in FIG. 3A.

Figure 8:
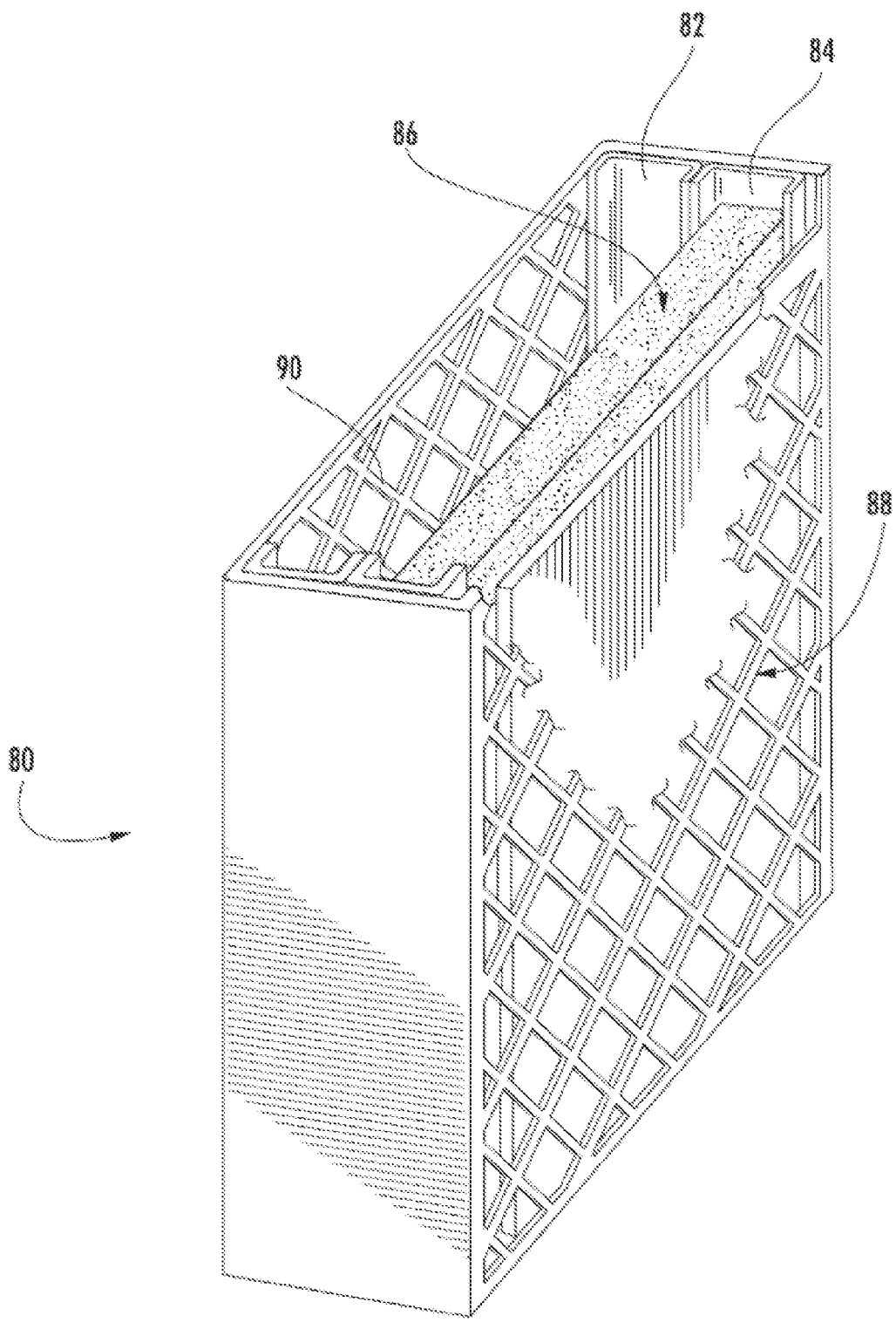
FIG. 8 provides a non-limiting depiction of an apparatus for preventing or delaying chill injury. The apparatus comprises a slotted chamber structure that permits the insertion and replacement of one or more catalyst module elements, as defined below. The outer layers of the physical structure may be composed of a material that permits air to flow into the catalyst.

FIG. 8 illustrates a catalyst structure 80 that includes two slots 82 and 84 for receiving a catalyst module (e.g. module 86). The catalyst module 86 is air-permeable and can be easily inserted into or removed from slot 84. Thus, the catalyst module 86 can be readily replaced if a new catalyst module is desired for use in the catalyst structure 80. The catalyst module 86 includes a catalyst such as described herein and that is preferably immobilized in a matrix. The catalyst structure 80 can include opposed air-permeable surfaces 88 and 90 such as mesh screens to allow air flow through the catalyst module 86. The catalyst structure 80 can, in alternative embodiments, include only one air-permeable surface, two non-opposed air-permeable surfaces or more than two air-permeable surfaces as would be understood to one of skill in the art. Although FIG. 8 includes two slots 82 and 84 for receiving a catalyst module (e.g. module 86), it would be understood to one of skill in the art that the catalyst structure 80 could include one or more slots for receiving a module. The catalyst structure 80 can be provided within a container used to transport a plant part such as fruit or flowers or can be affixed to a container, e.g., through the use of an adhesive layer as discussed herein.

The skilled artisan will further recognize that any of the methods, apparatuses, physical structures, compositions, or carriers disclosed herein can be combined with other known methods, apparatuses, physical structures, compositions, and carriers for delaying or accelerating a plant development process, particularly those processes generally associated with ethylene biosynthesis (e.g., chill injury response). Moreover, as described above, increased ethylene production has also been observed during attack of plants or plant parts by pathogenic organisms. Accordingly, the methods and apparatuses disclosed herein may find further use in improving plant response to pathogens.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

EXAMPLES

Example 1: Method of Delaying Chill Injury Response in Peaches

*Rhodococcus* sp DAP 96253 cultures were started from glycerol stocks stored at −80° C. by transferring 1 milliliter (ml) of the glycerol stock to 250 ml nutrient broth. The culture was incubated at 30° C. while shaking at 150 rotations per minute (rpm) for 2 days. Nutrient agar plates were inoculated and incubated for 2 days at 30° C.; cells from these plates were scrapped and used as an inoculum for YEMEA plates supplemented with glucose and the following additives: cobalt, urea, and asparagine. The YEMEA plates were incubated for a week at 30° C. The cells were scraped from the YEMEA plates and weighed (5-10 grams (g) of wet packed weight), a sample of the cells was taken and nitrile hydratase (NHase), amidase and ACC deaminase activities were determined.

Rhodococcal cells (5 g-10 g wet packed weight) were suspended in 10 ml of 50 millimolar (mM) phosphate buffer and transferred to a Petri dish which was placed in a brown paper bag containing 6 peaches that had been stored at 4° C. for 3 weeks. The bags were closed and left at room temperature for 7 days. This experiment was repeated three times.

Samples of peaches (10 g) were taken after exposure and transferred to 10 ml water in a 50 ml tube. The samples were crushed on ice and centrifuged for 10 minutes at 4,000 rpm. 1 ml samples were taken and transferred to microcentrifuge tubes and centrifuged for 10 minutes at 13,000 rpm. Samples were diluted 1:100, and were followed by a 1:10 dilution.

Glucose stock solution was prepared (1 mg/ml) and a standard solution of 100 ug/ml was prepared from the stock and used as a standard.

Anthrone reactions were carried out on the samples, standard, and negative control in glass test tubes by adding 5 ml of anthrone reagent (200 milligrams (mg) anthrone dissolved in 100 ml 75% sulfuric acid) to 1 ml of sample. The solution was mixed and placed in a water bath at 100° C. for 3.5 minutes. The tubes were allowed to cool and absorbance was read at 625 nm. The enzymatic activities for the rhodococcal cells are provided in Table 3.

TABLE 3

Enzymatic activities of rhodococcal cells used in the experiments.

| Media | NHase (units/mg cdw) | Amidase (units/mg cdw) | ACC deaminase (units/mg cdw) |
|---|---|---|---|
| G- | 2 | 0 | 0 |
| G Co | 81 | 0 | 0 |
| G U | 26 | 20 | 5 |

TABLE 3-continued

Enzymatic activities of rhodococcal cells used in the experiments.

| Media | NHase (units/mg cdw) | Amidase (units/mg cdw) | ACC deaminase (units/mg cdw) |
|---|---|---|---|
| G Co U | 70 | 4 | 1 |
| G Co U Asn | 60 | 10 | 3 |

G: Glucose;
Co: Cobalt;
U: Urea;
Asn: Asparagine

The data demonstrated that rhodococcal catalyst was effective in delaying the ripening of fruit after the fruit had been stored in the cold for an extended period (FIGS. 1-4). The catalyst was also able to prevent chill injury on the fruit. The properties of the peaches are provided in Table 4.

TABLE 4

Monitoring fruit ripening of control and catalyst treated peaches

| | Initial Measurements | | | After 7 days | | |
|---|---|---|---|---|---|---|
| | Brix after 3 weeks at 4° C. | pH | Degree of hardness | Brix | Carbohydrate content (mg/ml) | pH Comments |
| Control | 15.5 | 4 | ++++ | 18 | 167 | 4 + |
| G | 15.5 | 4 | ++++ | 16 | 146 | 4 ++ Several peaches had some degree of discoloration and fungal growth |
| G Co | 15.5 | 4 | ++++ | 17 | 136 | 4 +++ Two peaches were slightly wrinkled with a brown spot |
| G U | 15.5 | 4 | ++++ | 17 | 122 | 4 +++ One peach showed discoloration with some fungal growth |
| G Co U | 15.5 | 4 | ++++ | 17 | 127 | 4 +++ |
| G Co U Asn | 15.5 | 4 | ++++ | 17 | 132 | 4 +++ |

G: Glucose;
Co: Cobalt;
U: Urea;
Asn: Asparagine

Example 2: Method of Delaying Chill Injury Response in Bananas

The bananas are placed in the refrigerator at 15° C. for 4 weeks. After 4 weeks, the bananas are removed from the refrigerator and maintained at 25-27° C. in closed containers with moisture control. A select number of bananas are removed from the container and sprayed with catalyst or wrapped in catalyst impregnated paper. Once exposed to the catalyst, the bananas are placed back in the container and are observed for signs of chill injury response. The same procedure can be done with catalyst treatment before and after exposure to cold temperatures.

Example 3: Method of Delaying a Chill Injury Response in Soybean Plants

Soybean plants are grown in pots to a defined size with a defined number of leaves. The soybean plants are divided into two groups. The first group is the control group, and the second group is the leaf sprayed group with catalyst. The plants are exposed to temperatures of 4° C. for 12 hours. After exposure to cold temperatures, the plants are restored to room temperature (25-27° C.). The plants are observed for signs of chill injury response. The same procedure can be done with catalyst treatment before and after exposure to cold temperatures.

What is claimed is:

1. A method for delaying a chill injury response of a plant or plant part that exhibits a chill injury response comprising exposing the plant or plant part to one or more bacteria, wherein the one or more bacteria are exposed to the plant or plant part in a quantity sufficient to prevent or delay the chill injury response of the plant or plant part, where the plant or plant part is stored at a temperature of about 4 to 7° C. prior to, during, or after exposure to the one or more bacteria, and wherein the one or more bacteria are selected from the group consisting of *Rhodococcus* spp., *Brevibacterium ketoglutamicum*, *Pseudomonas chloraphis*, and combinations thereof.

2. The method of claim 1, wherein the plant or plant part is selected from the group consisting of a fruit, a vegetable, and a flower.

3. The method of claim 1, wherein the *Rhodococcus* spp. includes *Rhodococcus rhodochrous* DAP96253 strain, *Rhodococcus rhodochrous* DAP 96622 strain, *Rhodococcus erythropolis*, or combinations thereof.

4. The method of claim 1, wherein the one or more bacteria are induced to produce one or more enzymes by exposure to an inducing agent selected from the group consisting of urea, methyl carbamate, cobalt, asparagine, asparagine derivatives, glutamine, glutamine derivatives, and combinations thereof.

5. The method of claim 1, wherein the one or more bacteria are stabilized with a stabilizing agent.

6. The method of claim 5, wherein the stabilizing agent is trehalose.

7. The method of claim 1, wherein the one or more bacteria are fixed with glutaraldehyde and cross-linked.

8. The method of claim 7, wherein the glutaraldehyde-fixed bacteria are formulated into a spray.

9. The method of claim 1, wherein the one or more bacteria are provided in liquid form and the liquid is sprayed onto or near the plant or plant part.

10. The method of claim 9, wherein the liquid further comprises a liquid carrier.

11. The method of claim 10, wherein the liquid carrier is selected from the group consisting of an aromatic hydrocarbon, a substituted naphthalene, a phthalic acid ester, an aliphatic hydrocarbon, an alcohol, and a glycol.

12. The method of claim 1, wherein the one or more bacteria are provided in solid form and the solid is dusted onto or near the plant or plant part.

13. The method of claim 12, wherein the solid further comprises a solid carrier.

14. The method of claim 13, wherein the solid carrier is selected from the group consisting of a dust, a wettable powder, a water dispersible granule, and a mineral filler.

15. The method of claim 14, wherein the mineral filler is selected from the group consisting of a calcite, a silica, a talc, a kaolin, a montmorillonite, and an attapulgite.

16. The method of claim 12, wherein the one or more bacteria further comprises a hydrophobic fatty acid polyester coating, wherein the hydrophobic fatty acid polyester coating makes the one or more bacteria water resistant.

17. The method of claim 16, wherein the hydrophobic fatty acid polyester coating is a long chain fatty acid polyester derived from sucrose, sorbitol, sorbinose, glycerol, or raffinose.

18. The method of claim 1, further comprising exposing the plant or plant part to one or more exogenous enzymes, wherein the one or more exogenous enzymes are exposed to the plant or plant part in a quantity sufficient to prevent or delay the chill injury response of the plant or plant part.

19. The method of claim 18, wherein the one or more exogenous enzymes are selected from the group consisting of nitrile hydratase, amidase, asparaginase, ACC deaminase, cyanoalanine synthase-like enzyme, alkane monooxygenase, ammonium monooxygenase, methane monooxygenase, toluene dioxygenase, cyanidase, and combination thereof.

* * * * *